US008865431B2

(12) United States Patent  (10) Patent No.: US 8,865,431 B2
Dooley et al.  (45) Date of Patent: Oct. 21, 2014

(54) ANTIGEN BINDING DOMAINS

(75) Inventors: Helen Dooley, Baltimore, MD (US); Andrew Porter, Aberdeen (GB); Martin Flajnik, Baltimore, MD (US)

(73) Assignees: University of Maryland, Baltimore, MD (US); Aberdeen University, Aberdeen (GB)

( * ) Notice: Subject to any disclaimer, the term of this patent is extended or adjusted under 35 U.S.C. 154(b) by 21 days.

(21) Appl. No.: 13/280,837

(22) Filed: Oct. 25, 2011

(65) Prior Publication Data

US 2012/0064074 A1  Mar. 15, 2012

Related U.S. Application Data

(63) Continuation of application No. 10/486,608, filed as application No. PCT/GB02/03714 on Aug. 12, 2002, now abandoned.

(30) Foreign Application Priority Data

Aug. 10, 2001 (GB) .................................... 0119553.6
May 8, 2002 (GB) .................................... 0210508.8

(51) Int. Cl.
C12P 21/08 (2006.01)
C40B 30/04 (2006.01)
C12P 19/34 (2006.01)
C07K 16/40 (2006.01)
C40B 40/10 (2006.01)
C07K 16/00 (2006.01)

(52) U.S. Cl.
CPC ......... C07K 16/005 (2013.01); *C07K 2317/569* (2013.01); *C07K 2317/20* (2013.01); *C07K 2317/56* (2013.01); C07K 16/40 (2013.01); *C07K 2317/565* (2013.01)
USPC ............ 435/71.1; 435/71.2; 435/91.2; 506/7; 506/9

(58) Field of Classification Search
None
See application file for complete search history.

(56) References Cited

FOREIGN PATENT DOCUMENTS

EP  0368684  5/1990
EP  0954978  11/1999
WO  WO 94/25591  11/1994

OTHER PUBLICATIONS

French et al., "Development of a simple method for the recovery of recombinant proteins from the *Escherichia cloi* periplasm" Enzyme & Microbial Technology, 332-338, 1996.
Kabat et al., (1991) "Sequences of Proteins of immunological Interest", 5th Edition. National Institutes of Health, Betheseda, USA.
Wu & Kabat "An Analysis of the Sequences of The Variable Regions of Bence Jones Proteins and Myeloma Light Chains And Their Implications For Anti-Body Complementary" (1970) Journal of Experimental Medicine, 211-250.
United States Patent Office Action for U.S. Appl. No. 10/486,608 dated May 25, 2011 (8 pages).
United States Patent Office Action for U.S. Appl. No. 10/486,608 dated Sep. 3, 2010 (7 pages).
United States Patent Office Action for U.S. Appl. No. 10/486,608 dated Apr. 1, 2010 (6 pages).
United States Patent Office Action for U.S. Appl. No. 10/486,608 dated Dec. 29, 2008 (11 pages).
Conrath et al., "Camel Single-domain Antibodies as Modular Building units in Bispecific and Bivalent Antibody Constructs", J. Biol. Chern. 2001 276 ( 10) :7346-7350.
deBruin et al., "Selection of high-affinity phage antibodies from phage display libraries", Nature Biotechnology 1999 17:397-399.
Diaz et al. , "Mutational pattern of the nurse shark antigen receptor gene (NAR) is similar to that of mammalian lg genes and to spontaneous mutations in evolution:the translesion synthesis model of somatic hypermutation", International Immunology 1999 11 (5): 825-833.
Diaz et al. , "Somatic hypermutation of the new antigen receptor gene (NAR) in the nurse shark does not generate the repertoire: Possible role in antigen-driven reactions in the absence of germinal centers", Proc. Natl. Acad. Sci. USA 1998 95:14343-14348.
Diaz et al., "Evolution and the molecular basis of somatic hypermutation of antigen receptor genes", The Royal Society 2001 67-72.
Dooley and Porter, "Phage Display as a Tool to Investigate Antibody Repertoire Diversity:The Novel Antigen Receptor (NAR) of the Nurse Shark", Developmental and Comparative Immunology, 2000, 24(1) :S37-S38 (1 page).
Greenberg et al., "A new antigen receptor gene family that undergoes rearrangement and extensive somatic diversification in sharks", Nature 1995 374:168-173.
Greenberg et al., "A novel "chimeric" antibody class in cartilaginous fish:IgM may not be the primordial immunoglobulin", Eur. J. Immunol. 1996 26:1123-1129.
Hudson et al . , "Design, structure and applications of multimeric cancer-targeting scFvs and v-domain repertoires", Presentation at IBC' 11th Annual International Conference On Antibody Engineering, La Jolla, California, USA. Dec. 3-6, 2001. Published abstract and slide set which accompanied oral presentation.
Hudson et al . , "Multivalent ScFv Design Strategies for High Avidity and Rapid Tumor Targeting", Presentation at CHI'S Second International Conference, Baltimore, Maryland, USA. May 30 to Jun. 1, 2001. Published abstract and slide set which accompanied oral presentation.
Irving et al., "Genes to Proteins: Strategies for Screening Libraries of Gene-Protein Complexes", Symposium presented at The Genome Conference 2001, Lorne, Victoria, Australia. Feb. 11-15, 2001. Published abstract, slide set which accompanied oral presentation.
Krishnan et al. , Poster 1-67 Isolation of the "new antigen receptor" from Wobbegong sharks and expression of the Va domain in *E. coli*, The Genome Conference 2001, Lorne, Victoria, Australia. Feb. 11-15, 2001. Published abstract and poster presentation.

(Continued)

*Primary Examiner* — Gerald R Ewoldt
*Assistant Examiner* — Marianne Dibrino
(74) *Attorney, Agent, or Firm* — Michael Best & Friedrich LLP

(57) ABSTRACT

A process for the production of an antigen specific antigen binding domain using a transformed host containing an expressible DNA sequence encoding the antigen specific antigen binding domain, wherein the antigen specific antigen binding domain is derived from a variable region of the immunoglobulin isotype NAR found in fish.

15 Claims, 21 Drawing Sheets

(56) References Cited

OTHER PUBLICATIONS

Makela and Litman, "Lack of heterogeneity in antihapten antibodies of a phylogenetically primitive shark", Nature 1980 16;287(5783):639-640.

Muyldermans et al., "Recognition of antigens by single-domain antibody fragments: the superfluous luxury of paired domains", Trends in Biochemical Sciences 2001 26(4):250-.

Muyldermans S., "Single domain camel antibodies:current status", Reviews in Molecular Biotechnology 2001 74:277-302.

Nuttall et al., "Isolation of the new antigen receptor from wobbegong sharks, and use as a scaffold for the display of protein loop libraries", Molecular Immunology 2001 38:313-326.

Nuttall et al., "A naturally occurring NAR variable domain binds the Kgp protease from *Porphyromonas gingivalis*", FEBS Letters 2002 516:80-86.

Nuttall et al., "Immunoglobulin VH Domains and Beyond: Design and Selection of Single-Domain Binding and Targeting Reagents", Current Pharmaceutical Biotechnology 2000 1:253-263.

p. 308, p. 427 and p. 471 of the Oxford Dictionary of Biochemistry and Molecular Biology, Oxford University Press, Oxford:Published 1997.

Roux et al., "Structural analysis of the nurse shark (new) antigen receptor (NAR) :Molecular convergence of NAR and unusual mammalian immunoglobulins", Proc. Natl. Acad. Sci. USA 1998 95:11804-11809.

Schlom (Molecular and Cellular Research for Future Diagnosis and Therapy. S. Broder (Ed.), Williams and Wilkins, Baltimore, 1990, pp. 95-134).

Schluter et al., "Molecular origins and evolution of immunoglobulin heavy-chain genes of jawed vertebrates", Immunol. Today 1997 18 (11) : 543-549.

Science Direct. w.sciencedirect.com/science. 2009, 2 pages.

Watts et al., "Immune responses of teleost fish", Aust Vet J 2001 79 (8) :570-574.

```
                1                  10                  20                  30                  40                  50                  66       70
IgNAR I     ARVDQTPRSVTKETGESLTINCVLRDASYGLGSTCWYRKKSGSTNEESISKGGRYVETVNSGSKS
IgNAR II    -------QEI---------S--------D-CA-P--Y-N----------T--------------

13          ------------------------------A----------------------------------
34          ------------------------------A----------------------------------
25          ----------------------------N-A----------------------------------
50          ------------------------------A----------------------------------
19          ------------------------------A----------------------------------
17          ------------------------------A----------------------------------

80  abc           90       95                                          104         112
IgNAR I     FSLRINDLTVEDGGTYRCGVSPWGWGRSCDYPSCAQRPYAA                              CGDGTAVTVN
IgNAR II    ---------S---------K-YRKNWAYDCGLEELDWIYV                              Y-G--V----

13          ----------------------------------------STWCRTCCDYETGLCS*AYAA
34          ----------------------------------------GSWEPVTG*CAVNYAA
25          ----------------------------------------CTVMSLIFHLDRILSNLL*SNTD*DLIDCDNYAA
50          ----------------------------------------EPLVWSEL*HACSSPYAA
19          ----------------------------------------LNPTL*LLLCSCGSSIYAA
17          --------I-------------------------------LQLVWIPPL*LRLGGALPYGA                    --E---
```

Figure 2A

```
         1          10        20        30        40        50    66      70
IgNAR I  ARVDQTPRSVTKETGESLTINCVLRDASYGLGSTCWYRKKSGSTNEESISKGGRYVETVNSGSKS
IgNAR II ------QEI------S-------D-CA-P--Y-N--------T--------------------

47       ----------------------SNCVFSR--Y------------N-------WSIC*NN*PH*
05       ---------Q------------TET-S------------------------------------
04       ------------------------A---------------------------------------
21       ------------------------A---------------------------------------
39       ------------------------A---------------------------------------
01       ------------------------A---------------------------------------
08       ------------------------A---------------------------------------
07       ------------------------A---------------------------------------
15       ------------------------A---------------------------------------
42       ------------------------A---------------------------------------
43       ------------------------A---------------------------------------
22       ------------------------A---------------------------------------
27       ----KTIT-----------S-T-CAWD--Y------LD------T-------------E-T---
28       ----QTIT-----------SNCA-S--Y------------------------------------
37       ----QTI------Y-----Q-SIC---S--Y----R--P--L----------------------
14       ------------------------A-----------IGLNKRGEHIERWTIC*NS*QRIKV
```

Figure 2B

```
                  80    abc          90           95                      104            112
IgNAR  I     FSLRINDLTVEDGGTYRCGVSPWGWGRSCDYPSCAQRPYAA                   CGDGTAVTVN
IgNAR  II    ----------S------K--YRKNWAYDCGLEELDWIYV                    Y-G---V----

47     QRIKVLFFGNG*SMS*RKCHVSM*RGRYTPED*NNL                             ----------
05     --------------------------------PGIAGGSGCALLTLCCMRRWHCR          ---
04     --------------------------------WWEL*LRGALYMLHADMALP*L*
21     --------------------------------WIAGVDYDYSLAVLLSSTSMAMLHAEMALP*L*
39     --------------------------------EAHPLRSSVTTMLHAEMALP*L*
01     --------------------------------VFLADSWCGSVVTSCALPPMLHAEMALP*L*
08     --------------------------------IW*RCSLCLGCMLHAEMALP*L*
07     -------------------------L----I*MVCCCDSFGSVLYRRELHAEMALP*L*
15     --------------------------------CRTWGSRCDLAHVLLGCMRRWHCRDCE
42     --------------------------------AGI*LVEGSRGCMRRWHCRDCE
43     --------------------------------*RRI*LVWML*LTVCCMRRWHCRDCE
22     --------------------------------GVWICDETLSCALDRAACGDGTA*L*
27     -------------------------S------RAYPGL*LYCGYHGAL**IWRWHCRDCE
28     -------------------------S------KV*GYIGGLGVMYTEVALS*L*
37     ------------------------G---L-SAGGTPLCKLVPNQLAPDLTFRTTLMYTEMALP*L*
14     VLFEEN**SNS*RRWHVSLRCLDRLGAVTTYRCALPRGMLHAEMALP*L*
```

```
              80   abc        90           95                          104       112
IgNAR  I  FSLRINDLTVEDGGTYRCGVSPWGWGRSCDYPSCAQRPYAA                CGDGTAVTVN
IgNAR II  --------S---------K-YRKNWAYDCGLEELDWIYV                  Y--G---V----
40        -----------------------WGQLHVRCALGDAA                    ------------
46        -----------------------PDSWRFAVVCALEPDAA                 ------------
06        -----------------------CPHFSWCRLHEQCALA                  G-----------
02        ------H----------------CDSSIAVVAGCGYCLCTLVHSV             ------------
09        -----------------------ARAGGPFLCSCVYAA                   ------------
23        -----------------------PVGRSCDYPQLCSWGLNYAA              ------------
12        -----------------------STAGVDCDYTCALWDYAA                ------------
30        -----------------------SHAVAGGVCDYSSGLCSWSYAA            ------------
20        -----------------------SWAYSCDYLCSDEYAA                  ------------
38        -----------------------SLGARYSCDYNPCSSGYAA               --G--V------
18        -----------------------RIFLYSCDYACALDGYAA                ------------
26        ------T----------------ARPVGSCDYDLCSFRPYAA               ------------
49        -----------------------ELVWGYHSCDYDMCSFRYAA              ------------
24        -----------------------SLVWIGYIAVTTLDVLLRAA              ------------
31        -----------------------LAYTGRCGFCALDRLRKYAD              ------------
29        -----------------------CHRIAGVELAVTQVCALNRMYNYAA         ------------
36        ------I----------------QLEWSPAVTTSPAVLSRHAA              --G--V------
45        -----------------------SVYSWCPTVTGMVCSPYAA               ------------
03        -----------------------GGAYSCVTTYRGCALYYAA               ------------
32        -----------------------A--SSIAIRCDHAELCSRYGA             ------------
33        -----------------------AAATIQYSCDRLCSWDFAV               ------------
48        ------G-K---SW---------KAYTEPKTRRLIKCCRE                 Y-----------
16        --------S--------------K-PSRYSDCVRFELIDDV                Y-----------
11        --------S--------------RAELYCGAELDSFDE                   Y--G--V-----
41        --------S--------------K-SRCSTNLIG                       Y--G--V-----
44        --------S--------------A-KAEGMDREIRLNCVI                 Y--G--V-----
10        S-------A-S------------RLDLVCDETAYQDELEFDDI              Y-----------
```

Figure 2C cont'd

```
         1              10             20             30             40             50     66
IgNAR I  ARVDQTPRSVTKETGESLTINCVLRDASYGLGSTCWYRKKSGSTNEESISRGGRYVE
IgNAR II -------QEIT-------S-------D-CA-P-Y-N-------T-------

70   abc  80             90       95            100 bcdefghijklm 104        113
         TVNSGSKSFSLRINDLTVEDGGTYRCGVSPWGWGRSCDYPSCAQRPYAACGDGTAVTVNP
         ---------S---------K-YRKNWAYD-GLEELDWIY     VY-G---V----
```

Figure 3

```
ALA ARG VAL ASP GLN THR PRO ARG SER VAL THR LYS GLU THR GLY GLU SER LEU THR ILE ASN CYS VAL
GCT CGA GTG GAC CAA ACA CCG AGA TCA GTA ACA AAG GAG ACG GGC GAA TCA CTG ACC ATC AAC TGT GTC
CGA GCT CAC CTG GTT TGT GGC TCT AGT CAT CGT TTC CTC TGC CCG CTT AGT GAC TGG TAG TTG ACA CAG

LEU ARG ASP ALA SER TYR ALA LEU GLY SER THR CYS TRP TYR ARG LYS SER GLY GLU GLY ASN GLU
CTA CGA GAT GCG AGC TAT GCA TTG GGC AGC ACG TGC TGG TAT CGA AAA T

```
ALA ARG VAL ASP GLN THR PRO ARG SER VAL THR LYS GLU THR GLY GLU SER LEU THR ILE ASN CYS VAL
GCT CGA GTG GAC CAA ACA CCG AGA TCA GTA ACA AAG GAG ACG GGC GAA TCA CTG ACC ATC AAC TGT GTC
CGA GCT CAC CTG GTT TGT GGC TCT AGT CAT TGT TTC CTC TGC CCG CTT AGT GAC TGG TAG TTG ACA CAG

LEU ARG ASP ALA SER TYR ALA LEU GLY SER THR CYS TRP TYR ARG LYS SER GLY SER THR ASN GLU
CTA CGA GAT GCG AGC TAT GCA TTG GGC AGC ACG TGC TGG TAT CGA AAA TCG GGC TCA ACA AAC GAG
GAT GCT CTA CGC TCG ATA CGT AAC CCG TCG TGC ACG ACC ATA GCT TTT AGC CCG AGT TGT TTG CTC

GLU SER ILE SER LYS GLY GLY ARG TYR VAL GLU THR VAL ASN SER GLY SER LYS SER PHE SER LEU ARG
GAG AGC ATA TCG AAA GGT GGA CGA TAT GTT GAA ACA GTT AAC AGC GGA TCA AAG TCC TTT TCT TTG AGA
CTC TCG TAT AGC TTT CCA CCT GCT ATA CAA CTT TGT CAA TTG TCG CCT AGT TTC AGG AAA AGA AAC TCT

ILE ASN ASP LEU THR VAL GLU ASP GLY GLY TYR ARG CYS GLY LEU GLY VAL ALA GLY GLY TYR CYS
ATT AAT GAT CTA ACA GTT GAA GAC GGT GGC TAT CGT TGC GGT CTC GGG GTA GCT GGA GGG TAC TGT
TAA TTA CTA GAT TGT CAA CTT CTG CCA CCG ATA GCA ACG CCA GAG CCC CAT CGA CCT CCC ATG ACA

ASP TYR ALA LEU CYS SER SER ARG TYR ALA GLU CYS GLY ASP GLY THR ALA VAL THR VAL ASN
GAC TAC GCT CTG TGC TCT TCC CGC TAT GCT GAA TGC GGA GAT GGC ACT GCC GTG ACT GTG AAT
CTG ATG CGA GAC ACG AGA AGG GCG ATA CGA CTT ACG CCT CTA CCG TGA CGG CAC TGA CAC TTA
```

Figure 7

```
                   1          10         20         30          40         50     66      70
IgNAR I     ARVDQTPRSVTKETGESLTINCVLRDASYGLGSTCWYRKKSGSTNEEESISRKGGRYVETVN
HEL 5A7     ARVDQTPRSVTKETGESLTINCVLRDASYALGSTCWYRKKSGEGNEESISRKGGRYVETVN
HEL 5F11    ARVDQTPRSVTKETGESLTINCVLRDASYALGSTCWYRKKSGSTNEESISRKGGRYVETVN
            ****************************** ********** *.**** ***********

80         90              104        112
IgNAR I     SGSKSFSLRINDLTVEDGGTYRCGVSPWGWGRSCDYPSCAQRPYAACGDTAVTVN
HEL 5A7     SGSKSFSLRINDLTVEDGGTYRCGLGVAGG       YCDYALCSSR YAECGDTAVTVN
HEL 5F11    SGSKSFSLRINDLTVEDGGTYRCGLGVAGG       YCDYALCSSR YAECGDTAVTVN
            ************************:      *     ***.  *:..*  ** ********
```

Figure 8

```
ALA ARG VAL ASP GLN THR PRO ARG SER VAL THR LYS GLU THR GLY GLU SER LEU THR ILE ASN CYS VAL
GCT CGA GTG GAC CAA ACA CCG AGA TCA GTA ACA AAG GAG ACG GGC GAA TCA CTG ACC ATC AAC TGT GTC
CGA GCT CAC CTG GTT TGT GGC TCT AGT CAT TGT TTC CTC CCG CTT AGT GAC TGG TAG TTG ACA CAG

LEU ARG ASP ALA ASN TYR ALA LEU GLY SER THR CYS TRP TYR ARG LYS SER GLY SER THR ASN TRP
CTA CGA GAT GCG AAC TAT GCA TTG GGC AGC ACG TGT TGG TAT CGA AAA TCG GGC TCA ACA AAC TGG
GAT GCT CTA CGC TTG ATA CGT AAC CCG TCG TGC ACA ACC ATA GCT TTT AGC CCG AGT TGT TTG ACC

ASP SER ILE SER LYS GLY GLY ARG TYR VAL GLU THR VAL ASN SER GLY SER LYS SER PHE SER LEU ARG
GAC AGC ATA TCG AAA GGT GGA C

```
ALA ARG VAL ASP GLN THR PRO ARG SER VAL THR LYS VAL ALA GLY GLU SER LEU THR ILE ASN CYS VAL
GCT CGA GTG GAC CAA ACA CCG AGA TCA GTA ACA AAG GTT GCG GGC GAA TCA CTG ACC ATC AAC TGT GTC
CGA GCT CAC CTG GTT TGT GGC TCT AGT CAT TGT TTC CAA CGC CCG CTT AGT GAC TGG TAG TTG ACA CAG

LEU ARG ASP ALA ASN TYR PRO LEU GLY SER THR CYS TRP TYR ARG LYS SER LYS SER GLY SER THR ASN GLU
CTA CGA GAT GCG AAC TAC CCA TTG GGC AGT ACG TGC TGG TAT CGA AAA TCG AAA TCG GGC TCA ACA AAC GAG
GAT GCT CTA CGC TTG ATG GGT AAC CCG TCA T

```
                1                                           10                        20                        30                        40                        50        66        70
IgNAR I         ARVDQTPRSVTKETGESLTINCVLRDASYGLGSTCWYRKKSGSTNEESISKGGRYVETVN
Ova 4H11        ARVDQTPRSVTKETGESLTINCVLRDANYALGSTCWYRKKSGSTNWDSISKGGRYVETVN
Ova 3E4         ARVDQTPRSVTKVAGESLTINCVLRDANYPLGSTCWYRKKSGSTNEESISKGGRYVETVN
                *********** : ************ *** ************* *:************

80                        90                                  104              112
IgNAR I         SGSKSFSLRINDLTVEDGGTYRCGVSPWGWGRSCDYPSCAQRPYAACGDGTAVTVN
Ova 4H11        SGSKSFSLRINDLTVEDGGTYRCGREGRYHMDSCDYSRC  RYYAACGDGTAVTVN
Ova 3E4         SGSKSFSLRINDLTVEDGGTYRCGREGRYHMDSCDYSRC  RYYGACGDGTAVTVN
                ************************   *   ****  *  * *.***********
```

Figure 11

ANTIGEN BINDING DOMAINS

CROSS-REFERENCE TO RELATED APPLICATIONS

This application is a continuation of U.S. application Ser. No. 10/486,608 filed Sep. 1, 2004, which is a national stage entry of International Application No. PCT/GB02/03714 filed Aug. 12, 2002 now abandoned, which claims foreign priority benefits to United Kingdom Patent Application Nos. 0210508.8 filed May 8, 2002 and 0119553.6 filed Aug. 10, 2001, which are incorporated herein by reference in their entireties.

STATEMENT REGARDING FEDERALLY SPONSORED RESEARCH

This invention was made with government support under Grant Number RR006603 awarded by the National Institutes of Health. The U.S. government has certain rights in this invention.

The present invention relates to the production of antigen specific antigen binding domains (single domain antibodies) from fish, where the term fish encompasses both cartilaginous (subclass Elasmobranchii) and bony fish (class Osteichthyes). By antigen specific antigen binding domains we mean the variable region of a Novel Antigen Receptor (NAR).

Antibodies, especially monoclonal antibodies, are useful in, among other things, molecular diagnostics and therapeutics because of their high affinity binding and specificity. However, although it is now relatively simple to produce monoclonal antibodies using animal models the production of human monoclonal antibodies remains difficult. As will be appreciated, when monoclonal antibodies from non-human models are introduced into humans, the body mounts an immune response because the monoclonal antibody is foreign to the human system.

Recently, it has been appreciated that the activity of the monoclonal antibody can be retained while reducing the rejection thereof in humans by producing single domain antibodies (sda) from the variable chain of the relevant antibody. European patent application number 89311731.7 discloses such single domain antibodies and methods for the production thereof in mice.

Single domain antibodies are also important as they can penetrate tissues taking with them any linked compounds. In addition, they can bind within cavities on the surface of proteins, for example within enzyme binding sites thus disrupting function.

Single domain antibodies produced from Camelidae have been shown to recognize protein cavities and as such have the ability to inhibit enzymes (Lauwereys et al., *EMBO* 17 pp 3512-3520 1998).

Although the small size of single domain antibodies produced from Camelidae has allowed the recognition of protein cavities and inhibition of enzyme activity, the range of possible targets may still be relatively low, since many protein cavities may still be too small to be penetrable by single domain antibodies derived from Camelidae.

WO94/25591 and European patent application number 99200439.0 relate to the production of single domain antibodies from Camelidae heavy chain antibodies. Single domain antibodies produced from Camelidae heavy chain antibodies are more stable than mouse single domain antibodies and can be produced in larger quantities. However, as will be appreciated if, even the smaller members of the Camelidae family, for example llama, are to be kept in humane conditions they require significant areas of land to live upon.

An object of the present invention is to provide a process for the production of antigen specific antigen binding domains which seeks to alleviate the above problems.

A further object of the present invention is to provide a composition comprising antigen specific antigen binding domains for the inhibition of protein activity which seeks to alleviate the above problems.

According to an aspect of the present invention there is provided a process for the production of an antigen specific antigen binding domain, using a transformed host containing an expressible DNA sequence encoding the antigen specific antigen binding domain, wherein the antigen specific antigen binding domain is derived from a variable region of NAR found in fish.

It has been found that antigen specific antigen binding domains produced from the variable region of NAR found in fish are as stable as single domain antibodies produced from members of the Camelidae family.

Further many more fish can be kept per unit area than members of the Camelidae family.

The immunoglobulin isotype now known as NAR (Novel Antigen Receptor), was discovered in the serum of the nurse shark (*Ginglymostoma cirratum*) as a homodimeric heavy chain complex, naturally lacking light chains (Greenberg et al., *Nature* 374 pp 168-173 1995). However, before the present work by the inventors identification of NAR as an antigen binding domain was not fully appreciated neither was its ability to be raised against a specific antigen.

Only mammals (humans, mice, rabbits, sheep, camels, llamas, etc.) and some birds (chickens) were believed to be capable of something approaching a secondary immune response such as affinity maturation, antibody class switching etc. as a response to the presence of foreign antigen. For example, teleost fish (bony), which are much more advanced evolutionary than sharks, appear to rely solely upon the production of a low affinity, non-specific IgM type response (Watts et al., *Aust Vet J* 79 pp 570-574 2001). A defining characteristic of teleost IgM is their low affinity and ability to non-specifically bind multiple antigens. IgM neutralisation is through non-specific multiple binding, resulting mainly in agglutination, etc. Neutralisation without complement is usually associated with specific, high affinity binding and had not until this invention been seen in fish species. The antigen specific antigen binding domains of the present invention have been shown to neutralise activity of an enzyme immunogen directly without calling upon other components of the immune system.

The NAR variable (V) region conforms to the model of typical Ig superfamily domains with the predicted canonical, intradomain disulphide bond. However, whilst camelid VHH regions have up to 75% sequence identity with other mammalian VH regions, the identity between NAR V and conventional VH domains is as low as 25% (Roux et al., *Proceedings of the National Academy of Sciences. USA* 95 pp 11804-11809 1998).

Due to this low identity and lack of NAR sequences in the Kabat database, the amino acids of NAR V regions have previously been numbered sequentially (Roux et al., *Proceedings of the National Academy of Sciences. USA* 95 pp 11804-11809 1998). To enable easy comparison of residues in different NAR V molecules, or NAR V region sequences with those of other species during this work, a numbering system was derived for NAR V region based upon that of Kabat et al., (1991) (*Sequences of Proteins of immunological*

Interest, 5*th* Edition. *National Institutes of Health, Bethesda, USA*). (Note: this numbering system is used in the Figures attached hereto).

Immediately apparent from the alignment is the deletion of a large portion of CDR2 (residues 54-65) giving the NAR V region its characteristically small size (see, for example, FIG. 2A).

Initial sequence analysis allowed the classification of NAR V domains into two closely related classes (type I or II), both being constructed from one V, three D and one J segment. Type I regions have non-canonical cys residues in Fr2 (C35) and Fr4 (C103), which likely form a domain-stabilising disulphide bond. In longer NAR CDR3 loops additional cysteine residue pairs have been observed and almost certainly form disulphide bridges within the CDR, as is found in some cattle VH domains with an unusually long CDR3.

Type II regions are very similar in overall structure to type I but instead have non-canonical cysteine residues located in Fr1 (C29) and CDR3, which are proposed to form a constraining disulphide bond like that observed in camelid VHH domains. The presence of cysteines within each NAR type is shown in schematic form in FIG. 1.

Recently, an additional NAR type has been identified as the predominant expressed form in nurse shark pups (Type III) but due to its germline joined state displays no junctional diversity.

In type I and II NAR the DNA encoding the V region is generated by the physical joining of DNA segments which are spatially separate in the genome. This joining process occurs in B-cells and helps generate the diversity of sequence seen for these NAR types. For type III these DNA segments are already physically joined in the DNA of all cells, hence the term germline joined.

NAR possesses the cluster type genomic organisation usually observed for Ig receptors in cartilaginous fish, but less than five NAR loci are thought to exist, with only two or three being capable of functional rearrangement and expression. The diversity observed in the primary repertoire is generated through recombination mechanisms and, although extensive (due to the presence of three D segments), is localised to CDR3. On encounter with antigen this repertoire is rapidly expanded by extensive mutation. The pattern of mutation in NAR is unlike that observed in shark IgM, which shows low levels of mutation and poor clustering to CDRs, but rather bears the hallmarks of mammalian-like somatic mutation.

It has recently been found that NAR V is similar to VH, VL and TCR V but distinct from all three, hence its "unique domain architecture". The VH name has been used in the past because the constant portion of NAR is a heavy chain but the V region is actually more like VL/TCR V than VH (i.e. groups closer on a phylogenetic tree). NAR V is not like the camel VHH domains which are derived from bona fide heavy chain V regions. The antigen binding domain of the NAR is closer to a VL domain naturally lacking VH rather than the other way round.

The sequence alignment of NAR V and camel VHH clearly shows the huge difference in sequence. If NAR V and camel VHH have the same physical structure (which has been implied but not proven) they achieve this using completely different amino acid sequences, and one would not be able to amplify a NAR V region library using camel VHH library primers. In addition, the ways in which the NAR V and camel VHH gene repertoires are created during VDJ joining are different due to the organisation of the immunoglobulin genes (Schluter et al Immunol Today 18 pp 543-549 1997).

Preferably the transformed host is a prokaryote or a lower eukaryote.

There are many established prokaryote and lower eukaryote hosts. These hosts are known to correctly express foreign proteins.

Conveniently the prokaryote host is *Escherichia coli*.

In preferred embodiments the expressible DNA sequence is in the form of a phagemid vector.

Phagemid expression has advantages over phage genome expression in that it results in greater genetic stability and the bacterial transformation efficiency is higher thus enabling the construction of potentially larger and more diverse libraries.

To display antibody fragments on phage the gene encoding the variable region of the antibody can be fused to that of a phage surface protein, usually gene III or VIII. Gene III fusion is favoured due to its limited copy number (3-5 copies) on the tip of each phage, minimising possible avidity effects which are undesirable when trying to isolate binders of high affinity. The antibody fragment genes can be cloned directly into the phage genome or fused to gene segments present within phagemid plasmids.

Preferably the fish is a member of the Elasmobranchii subclass, for example, a shark or a dogfish.

A greater number of smaller members of the Elasmobranchii subclass can be kept in tanks which are smaller in unit area than the grazing area required for the same number of members of the Camelidae family. As the members of the Elasmobranchii subclass are kept in tanks they can easily be caught for extraction of their blood.

Conveniently the shark is a nurse shark, *Ginglymostoma cirratum*.

Preferably the antigen specific antigen binding domain has a specific specificity. Accordingly, the antigen specific antigen binding domain can be targeted to a specific antigen(s).

Conveniently the antigen specific antigen binding domain is monoclonal. In this connection, the antigen specific antigen binding domain is raised to a single antigen.

In preferred embodiments the specificity of the antigen specific antigen binding domain is determined by an antigen which is introduced into the chosen fish.

According to a further aspect of the present invention there is provided a process for the production of an antigen specific antigen binding domain comprising the steps of:
a) immunising a fish with an antigen;
b) isolating lymphocytes from the fish;
c) isolating RNA for an antigen specific antigen binding domain from the lymphocytes;
d) amplifying DNA sequences encoding the antigen specific antigen binding domain by PCR;
e) cloning the amplified DNA into a display vector;
f) transforming a host to produce a library;
g) selecting the desired clones from the library;
h) isolating and purifying the antigen specific antigen binding domain from these clones;
i) cloning the DNA sequences encoding the antigen specific antigen binding domain into an expression vector;
j) transforming a host to allow expression of the expression vector.

Screening of displayed libraries for specific binding sites involves repeated cycles of selection with the desired antigen in the process of biopanning. Generally during selection, the library of phage displayed antigen binding, domains is incubated with immobilised antigen, unbound phage are washed out and bound phage eluted. This selected population is expanded by bacterial infection and put through further rounds of selection. As each phage encapsulates the DNA encoding the V region it displays, there is a functional linking of genotype and phenotype, reminiscent of membrane bound immunoglobulin on the surface of B-cells. Such cyclic panning has thus proven able to enrich for clones of high affinity, much like in vivo antibody selection.

Preferably before step d) the cDNA of the antigen binding domains is generated.

Conveniently restriction enzymes are used to digest the amplified DNA sequences encoding the antigen specific antigen binding domain. The restrictions enzymes can be chosen depending upon, for example, the handle of the primers used in the above process.

In preferred embodiments the restriction enzymes are NcoI and NotI.

Conveniently the display vector is any phagemid vector, for example, pHEN2.

Preferably the expression vector is a soluble expression vector such as pIMS100.

The above vectors are merely examples of the vectors which can be used. It is common general knowledge to those skilled in the art which vectors can be used.

According to a further aspect of the present invention there is provided an antigen specific antigen binding domain produced by the process as defined above.

According to a yet further aspect of the present invention there is provided a composition for the inhibition of protein activity comprising antigen specific antigen binding domains derived from a variable region of the immunoglobulin isotype NAR found in fish.

Despite the fact that the NAR V region is 12 kDa which is 20% smaller than any 15 kDa single domain antibody derived from Camelidae, it was still possible to alter protein activity therewith. Size is a significant factor in the therapeutic applications of antigen specific antigen binding domains and other single domain antibodies, with therapeutic benefits of increased tissue penetration, better access to protein clefts for neutralisation via steric hindrance and reduced immunogenicity, resulting from the use of antigen specific antigen binding domains of the present invention.

Antigen specific antigen binding domains derived from NAR therefore have a wider target population than single domain antibodies derived from Camelidae by virtue of their smaller size. The potential for immunogenicity is also reduced since in general the smaller the size of a protein the less the immunogenicity.

Furthermore, although NAR sequences have, in work previous to that of the inventors, been identified at the DNA level, there has been no clue from the DNA evidence that a somatically maturable repertoire, capable of selecting high affinity, specific binders could be a characteristic of the NAR response. Hence, it is unexpected to be able to generate an NAR library of antigen binding domains derived from sharks and the selection from this of specific and functional antigen specific antigen binding domains and their corresponding receptor genes. Sequencing of these genes confirms that an atypical (for fish and organisms of this evolutionary lineage) somatically-maturable (showing mutation from the germ line repertoire) response occurs within the NAR repertoire, driven by the immunisation process. This has resulted in the selection of highly specific, high affinity antigen binding domains capable of antigen neutralisation in isolation and not the expected non-specific, low affinity IgM like response typically found in fish and sharks.

Further still, the inventors have been able to isolate NAR antigen specific antigen binding domains and demonstrate for the first time that the NAR V is able to fold and function in isolation from the rest of the molecule (and in a non-shark environment), that the antigen specific antigen binding domain matures from the germ line genes to become specific for antigen (only possible with a library derived from mRNA and not DNA) and that the antigen specific antigen binding domain is able to bind specifically to the immunising antigen.

In summary, as described below, the inventors have been able to immunize a shark and derive from this immunization a specific, somatically matured antigen specific antigen binding domain that is of high affinity and specific for the immunogen. In addition, the antigen specific antigen binding domain is able to neutralise the activity of the immunogen directly, without calling upon other components of the immune system. According to previous understandings, this should not have been possible for a primitive species such as sharks.

Conveniently, a composition is provided wherein the antigen specific antigen binding domain is a product of the process as defined above.

Preferably inhibition of protein activity is in a concentration dependent manner.

Preferably, the composition further comprises a pharmaceutical carrier or diluent therefor.

Such pharmaceutical carriers are well known in the art.

According to a further aspect of the present invention, there is provided an antigen specific antigen binding domain produced from a variable region of NAR.

The invention will now be described, by way of illustrate on only, with reference to the following examples and the accompanying figures.

FIGS. 2A, 2B and 2C show the amino acid translations of the sequences obtained in the Examples (SEQ ID. 1 to 51). The sequences are aligned against a typical type I and type II clone sequence (top of each Figure with CDR's highlighted in bold) dashes indicate identity to the type I clone and * indicates an in-frame stop codon.

FIG. 3 shows NAR type I and II variable region amino acid sequence alignment (SEQ 1 and 2). Germline sequence is given for type I, whilst that given for type II is typical of those observed from somatically mutated cDNA sequences (Roux et al., *Proceedings of the National Academy of Sciences. USA* 95 pp 11804-11809 1998). Sequence identity is indicated by a dash and the CDR's of both sequences are in bold. The numbering above the sequences was generated by comparison of conserved residues (underlined) with those of other species and is used to enable comparison of NAR V region sequences.

Figure 1:
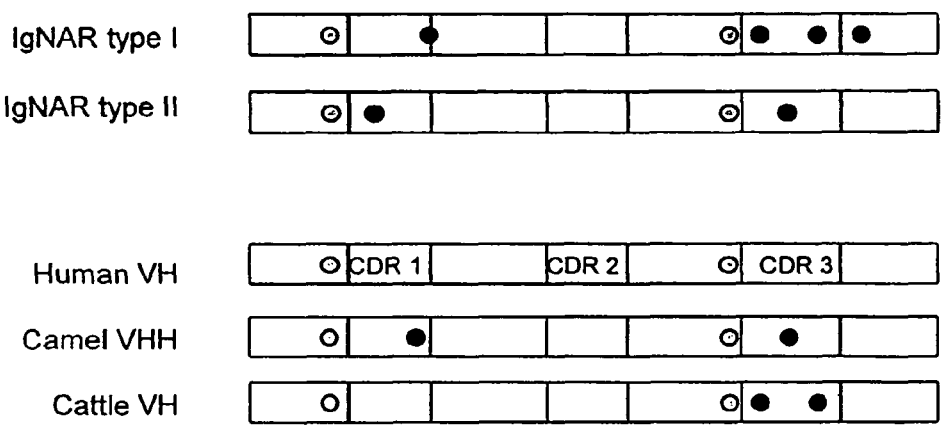
FIG. 1 shows the presence of cysteine amino acid residues within each NAR type, and human, cattle and camel variable regions for comparison. Canonical cysteines are shown by ○ and non-canonical cysteines are shown by ●.
Figure 4:
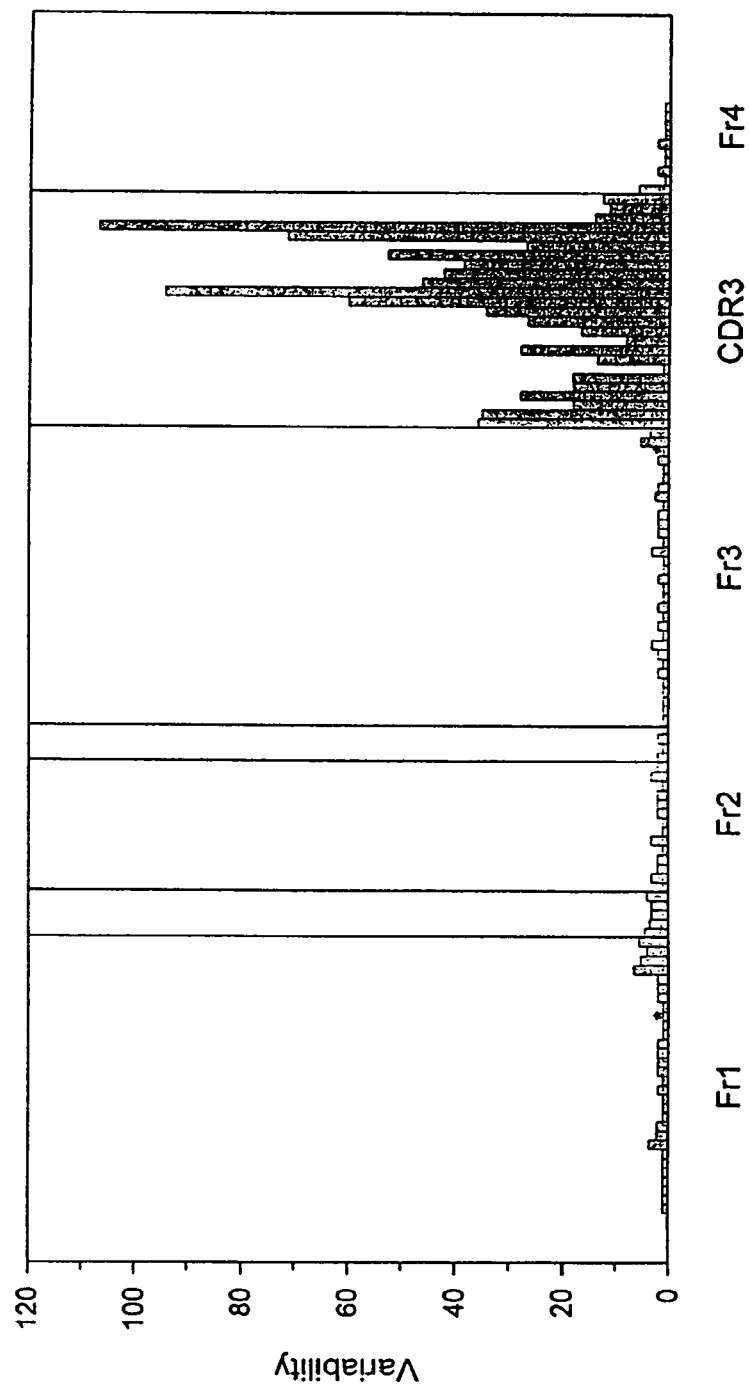

FIG. 4 shows a variability plot for the 29 immune library sequences identified in the Example (pre-selection and functional). Variability at each position was calculated according to the method of Wu & Kabat (1970)(*Journal of Experimental Medicine* 132 pp 211-250). The canonical cysteine residues, C22 and 92, are marked by an asterisk.

Figure 5A:
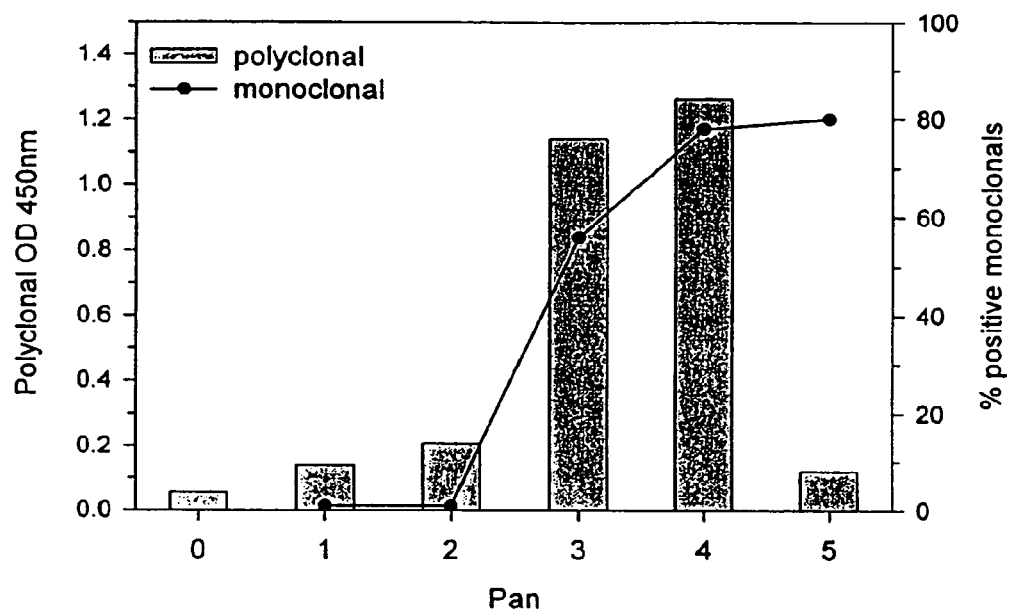
Figure 5B:
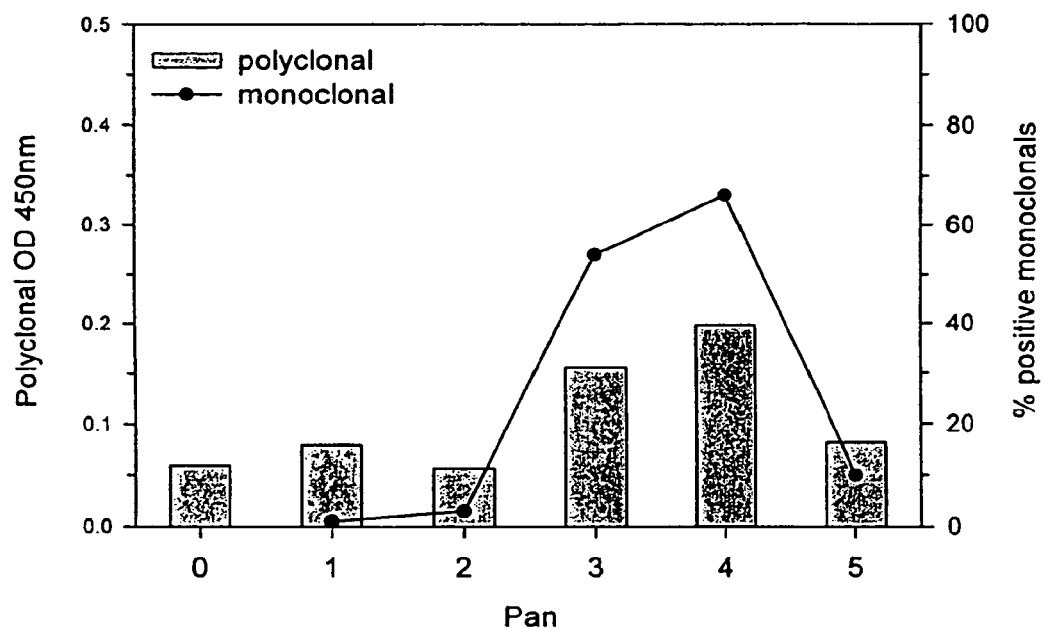

FIGS. 5A and B show polyclonal and monoclonal phage ELISA results for selection on Hen egg white lysozyme (HEL)(FIG. 5A) and Chicken ovalbumin (Ova)(FIG. 5B). Phage numbers were normalised for each pan prior to polyclonal analysis. Data presented is a mean of triplicate wells and representative of at least three assays. Monoclonal results are percentages obtained from 96 clones for each pan.

FIG. 6 shows the DNA (SEQ ID. 53 & 54) and encoded amino acid sequence (SEQ ID. 52) of the α-HEL 5A7 clone. CDRs are highlighted in bold.

FIG. 7 shows the DNA (SEQ ID. 56 & 57) and encoded amino acid sequence (SEQ ID. 55) of the α-HEL 4F11 clone. CDRs are highlighted in bold.

FIG. 8 shows the amino acid alignment of the two α-HEL clones, 5A7 (SEQ ID. 52) and 4F11 (SEQ ID. 55), with a typical type I clone (SEQ ID. 1). Sequences are numbered according to FIG. 3 for ease of comparison, differences between the selected clones are highlighted in underlined and CDR's are highlighted in bold, * conserved residues in all sequences, : conserved substitutions, . semi-conserved substitutions.

FIG. 9 shows the DNA (SEQ ID. 59 & 60) and encoded amino acid sequence (SEQ ID. 58) of the α-Ova 4H11 clone. CDRs are highlighted in bold.

FIG. 10 shows the DNA (SEQ ID. 62 & 63) and encoded amino acid sequence (SEQ ID. 61) of the α-Ova 3E4 clone. CDRs are highlighted in bold.

FIG. 11 shows amino acid alignment of the two α-Ova clones, 4H11 (SEQ ID. 58) and 3E4 (SEQ ID. 61), with a typical type I clone (SEQ ID. 1). Sequences are numbered according to FIG. 3 for ease of comparison, differences between the selected clones are underlined and the CDR's are highlighted in bold. * conserved residues in all sequences, : conserved substitutions, . semi-conserved substitutions.

Figure 12:
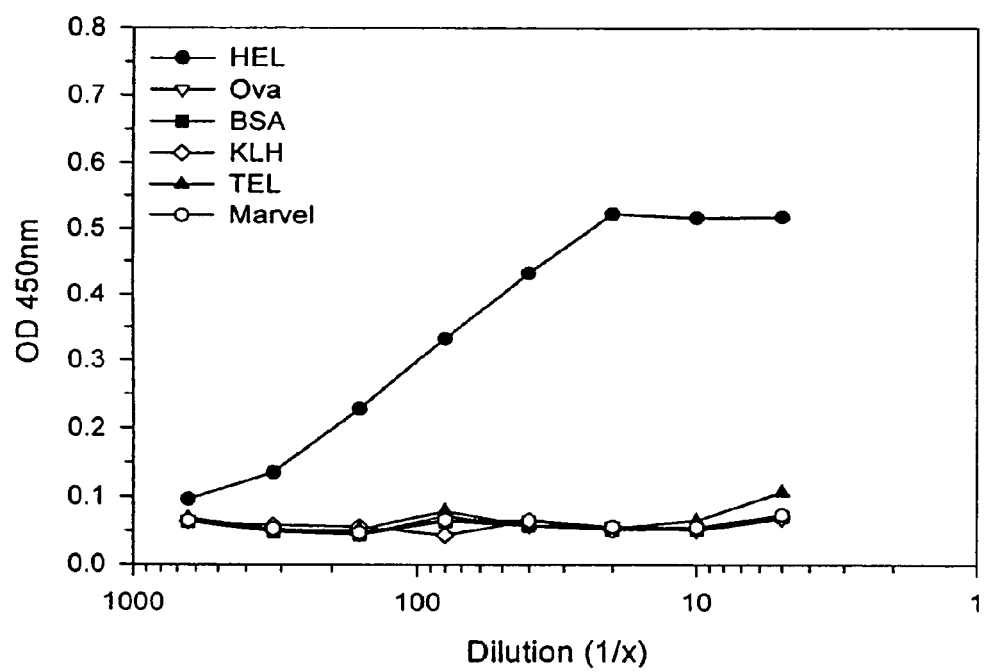

FIG. 12 shows binding analysis of α-HEL clone 5A7. Serial dilutions of crude periplasmic release solution were applied to an ELISA plate coated with each of the test proteins at 10 μg/ml and blocked with Marvel. Data presented is a mean of triplicate wells and representative of at least three repeat assays.

Figure 13:
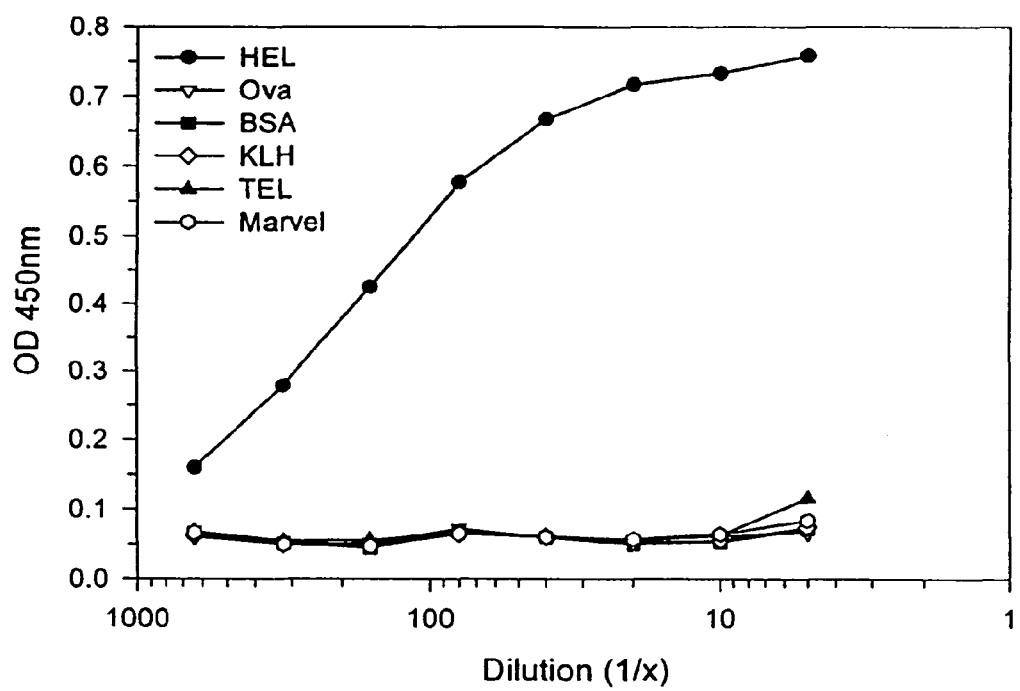

FIG. 13 shows binding analysis of α-HEL clone 4F11. Serial dilutions of crude periplasmic release solution were applied to an ELISA plate coated with each of the test proteins at 10 μg/ml and blocked with Marvel. Data presented is a mean of triplicate wells and representative of at least three repeat assays.

Figure 14:
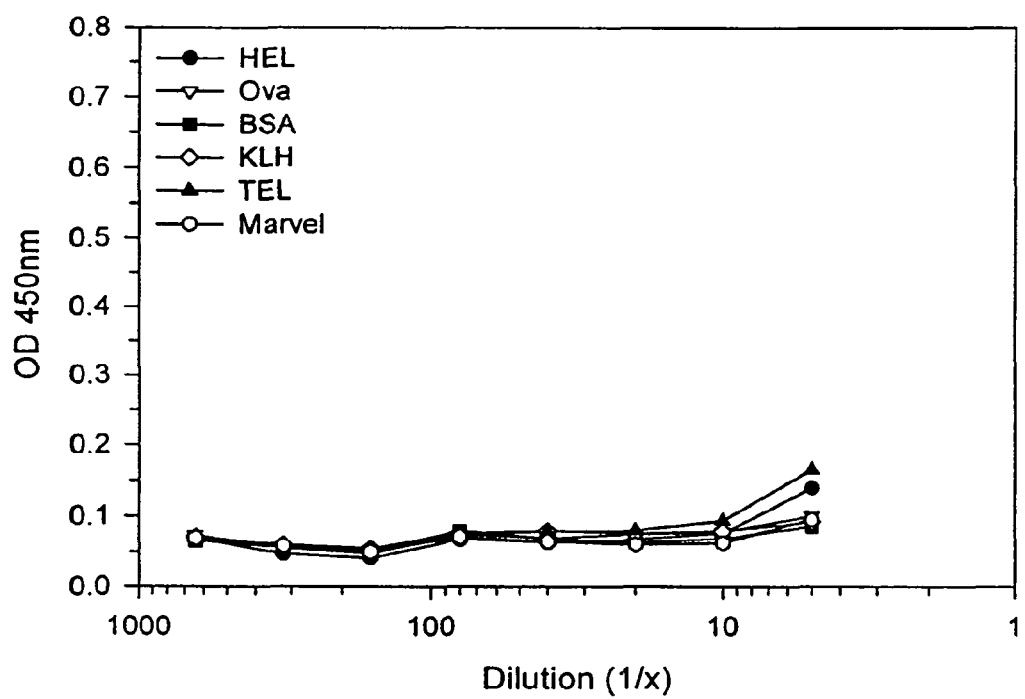

FIG. 14 shows binding analysis of α-Ova clone 4H11. Serial dilutions of crude periplasmic release solution were applied to an ELISA plate coated with each of the test proteins at 10 μg/ml and blocked with Marvel. Data presented is a mean of triplicate wells and representative of at least three repeat assays.

Figure 15:
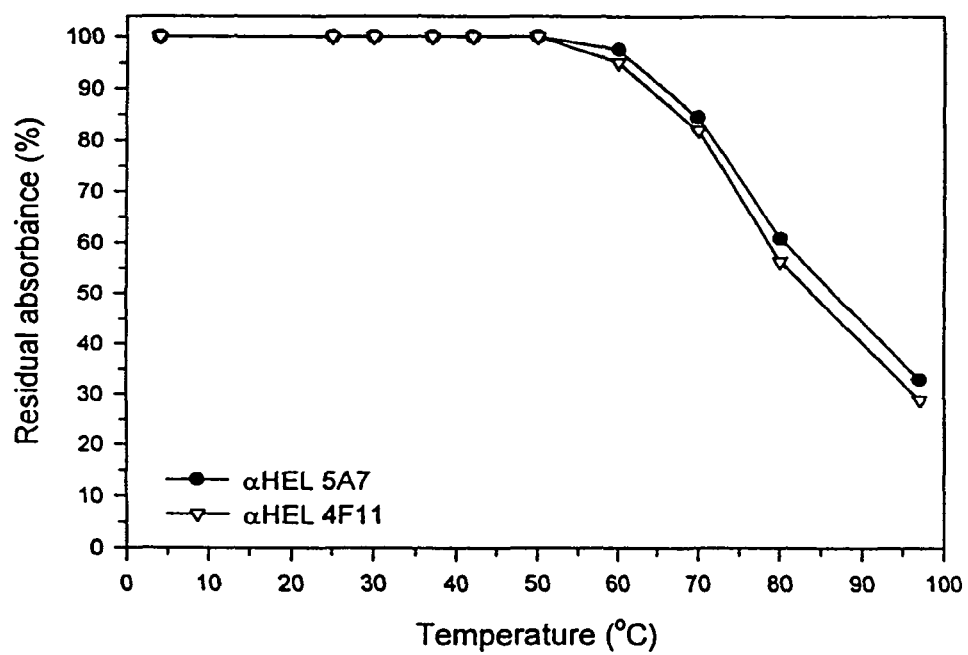

FIG. 15 shows a comparison of the stability of the anti-HEL clones 5A7 and 4F11 to irreversible thermal denaturation. Data presented is a mean of triplicate wells and representative of at least three repeat assays.

Figure 16:
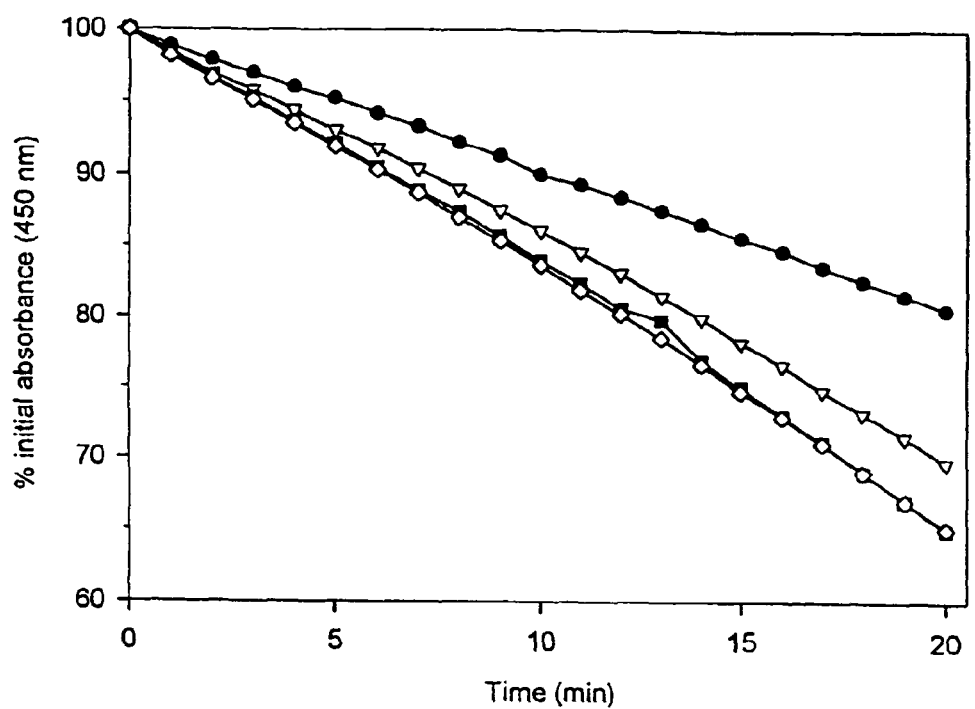

FIG. 16 shows a lysozyme enzymatic inhibition assay. Purified HEL-5A7 NAR V region protein at a final concentration of 2500 nM (filled circle), 250 nM (open triangle) or 25 nM (filled square) were pre-incubated with HEL prior to the introduction of *M. lysodeikticus* bacterium. The control wells (open diamond) contained buffer in place of HEL-5A7 protein. The data presented is an average of 3 replicates and a typical data set from three repeat experiments.

EXAMPLE

Bacterial Strains

The electroporation-competent strain *E. coli* XL1-Blue {recAl endA1 gyrA96 thi-1 hsdR17 supE44 relA1 lac [F' proAB lacI$^q$ ZΔM15 Tn10 (Tet$^r$)]} (Stratagene Ltd.) was used to prepare and pan the NAR V region phage display libraries.

PCR Materials

All custom oligonucleotides used throughout this work were ordered from Sigma-Genosys Ltd., and were desalted and/or HPLC purified. Library primer sequences were as follows (all 5' to 3'):

```
NAR F4For1
                                        (SEQ ID. 64)
ATA ATC AAG CTT GCG GCC GCA TTC ACA GTC ACG
ACA GTG CCA CCT C

NAR F4 For2
                                        (SEQ ID. 65)
ATA ATC AAG CTT GCG GCC GCA TTC ACA GTC ACG
GCA GTG CCA TCT C

NAR F1 Rev
                                        (SEQ ID. 66)
ATA ATA AGG AAT TCC ATG GCT CGA GTG GAC CAA
ACA CCG
```

All PCR reactions were performed on a Hybaid PCR sprint block in Hybaid 0.2 ml thin-walled omnitubes.

Construction of NAR V Region Libraries for Phage Display

RNA Preparation

To enable production of the immune library, three nurse sharks were immunised five times with Hen egg-white lysozyme (HEL) (over a period of approximately 8 months). Blood samples were taken from each shark following each immunisation, peripheral blood lymphocytes isolated, and total RNA prepared for each bleed. The RNA from bleeds 4 and 5 for each of the three sharks was pooled and stored at −80° C. until required for cDNA synthesis.

cDNA Synthesis and PCR Amplification

For cDNA synthesis, ready-to-go RT-PCR beads (200 μM each dNTP, 10 mM Tris-HCl buffer, 60 mM KCl, 1.5 mM $MgCl_2$, M-MuLV reverse transcriptase, RNAGUARD7, RNase/DNase free BSA and 2 U Taq DNA polymerase) (APB Ltd.) were reconstituted in 45 μl of DEPC treated $H_2O$ by incubating on ice for 5 min or until the beads were completely dissolved. To each tube 2 μl of nurse shark tRNA at 2 μg/μl and 2 μl of NAR F4 For primer or F4 For2 primer at 25 pM/μl were added. Both of these primers are specific for NAR framework region 4 and have a NotI site incorporated in the handle to allow subsequent cloning into the phagemid vector. Tubes were flicked gently to mix contents and incubated on a PCR block pre-warmed to 46° C. for 30 min. Following cDNA synthesis, tubes were incubated at 95° C. for 7 min to inactivate the reverse transcriptase and denature the template.

To each tube 2 μl of the common primer NAR F1 Rev at 25 pM/μl, containing a NcoI site in its handle was added, tubes were pre-heated to 95° C. and 1 μl of Taq DNA polymerase at 1 U/μl added to each prior to cycling 32 times at 95° C. for 2 min, 55° C. for 1 min and 72° C. for 1 min 30 s.

Following PCR amplification type I and type II, products were PAGE purified on a 1.5% gel a strong band was visualised at approximately 400 bp for both primer sets indicating successful amplification of the NAR V region.

Cloning of NAR V Region into the Phagemid Vector pHEN2

PAGE-purified PCR product was digested with NcoI and NotI restriction enzymes, at the sites incorporated by the handled primers used for amplification, to allow cloning into the phagemid vector pHEN2. Restricted DNA was purified on a 1.5% agarose gel and the DNA excised and cleaned.

Plasmid DNA, harvested from an overnight culture of *E. coli* XL1-Blue and phenol:chloroform treated, was similarly cut with NcoI and NotI restriction enzymes. Double-cut vector was purified on a 0.7% agarose gel and DNA extracted. For library construction digested vector was not treated with calf alkaline phosphatase.

To enable quantification, 2 μl of suitably digested PCR product and pHEN2 vector were run on a 1% agarose gel against 2 μl of DNA marker VI (Boehringer Ltd.) and band intensities evaluated by eye to judge relative amounts of DNA present. Ligations were performed with equal amounts of vector and insert DNA in the presence of 2.5 μl of 10× ligase buffer and 1 μl of T4 ligase. The final volume was made up to 25 μl with H$_2$O and incubated overnight at 15° C. For library construction 30-40 such ligations were performed.

Following incubation overnight, ligation products were pooled, phenol:chloroform cleaned and the resultant DNA pellet reconstituted in approximately 100 μl of 1:10 dilution of 10 mM Tris-HCl, pH 8.5. DNA was then ready for transformation into electroporation-competent cells.

Transformation of Electroporation-Competent Cells and Evaluation of the Resultant Library Ligated DNA was aliquotted into chilled electroporation cuvettes and to each 40 μl of freshly thawed electroporation-competent XL1-Blue cells was added. Cells were electroporated and resuspended in 100 μl ice-cold 2×TY media with 1% glucose (w/v) added. Dilutions at $10^{-2}$, $10^{-4}$ and $10^{-6}$ were performed for each transformation and plated on TYE agar containing 100 μg/ml ampicillin and 1-2% glucose (w/v). The remaining bacterial suspension was plated straight onto 140 mm petri-dishes containing TYE with ampicillin and glucose (as above). All plates were grown overnight at 37° C.

Following incubation overnight, colonies from the dilution plates were counted to give an estimate of the final library size, approximately $5 \times 10^6$ members. Approximately 100 individual colonies were PCR screened using 1 μl each of the primers LMB3 (5' CAGGAAACAGCTATGAC 3') (SEQ ID. 69) and pHEN seq (5' CTATGCGGCCCCATTCA 3') (SEQ ID. 70) at 25 pM/μl, 1 μl of dNTPs at 25 pM each, 2 μl of 50 mM MgCl$_2$, 5 μl of 10×Taq polymerase buffer, 1 μl Taq polymerase (at 1 U/μl) and 39 μl Steripak H$_2$O. PCR was undertaken as follows; 1 cycle at 95° C. for 3 minutes (to lyse bacteria) and 20 cycles of 95° C. for 1 min, 55° C. for 1 min and 72° C. for 1 min. PCR product was run on a 1.5% agarose gel containing EtBr against molecular weight marker VI (Boehringer Ltd.) to evaluate the percentage of the library carrying NAR V region insert. Using this method, 75% of the library was observed to be carrying an insert approximating that expected for the NAR V region, giving a functional library size of $3.75 \times 10^6$ members. Fifty clones, established in this way to be carrying correctly sized inserts, were then sequenced to evaluate library diversity.

The encoded amino acid translations of the sequences obtained are shown in FIGS. 2A, B and C.

Of the 50 clones sequenced, 6 were found to harbour one or more stop codons encoded by an in-frame TGA codon within CDR3. In the case of clones 13 and 19 the stop codon is probably a consequence of the D3 and D2 segments (respectively) being utilised in a non-preferred reading frame (Roux et al., Proceedings of the National Academy of Sciences. USA 95 pp 11804-11809 1998). The reason for the stop codons in the other 5 clones is less distinct but is likely due to somatic hypermutation within this region.

A further 15 clones carried frameshift mutations leading to the production of non-sense or truncated proteins. For the majority of these clones the frameshift occurred within CDR3, possibly as a consequence of nucleotide addition or deletion during the recombination process. For clones 14 and 41 the frameshift mutation arose within Fr2 (position 41 according to FIG. 3) and Fr3 (position 67) respectively and are more likely due to polymerase errors during library construction (the frameshift in clone 14 occurs immediately after a long poly-A tract in the DNA sequence).

The sequence alignment and the variability plot of the 28 clones encoding functional inserts (FIGS. 2 and 4) show good diversity, with each clone having a unique amino acid sequence. Variability is seen to be focussed across CDR3 which, like clones from a similarly constructed naïve library, varied greatly in both sequence and length. The immune nature of the library is important as NAR V regions which bound to antigen could not be isolated from a naïve library (ie. without prior immunisation).

Both NAR types were represented, with approximately 80% being type I and 20% type II, however a number of clones proved difficult to assign to an NAR type. For example, clone 33 has a type II Fr1 but type I CDR3 and Fr4, whilst clones 06, 40 and 46 have a type I Fr1 and CDR3 but a type II Fr2 and Fr4. This finding suggests the possibility that gene conversion may be occurring between the NAR genes.

A number of other clones also show some atypical features which were not observed with the naïve library pre-selection clones. Clones 24 and 36 are both assigned as type I on the basis of other sequence characteristics but do not carry the pair of cysteine residues normally observed in the type I CDR3. The clones 06, 40, 46 and 48 all encode an uneven number of cysteine residues. As mentioned previously in the case of 06, this may be due to gene conversion. Very few clones bearing an uneven number of cysteines have been observed previously and so it is thought that the V region must be under considerable pressure to maintain an even number of cysteine residues, enabling formation of disulphide bonds. The consequence of unpaired cysteines within the NAR V region is, as yet, unknown but may be detrimental to domain folding. If this is indeed the case then such clones will probably be eliminated from the library during early pans due to their toxicity to the expressing bacteria.

Clone 02 encodes 4 cysteine residues in its CDR3, giving this V region a total of 8 cysteine residues and the potential to form 4 disulphide bonds. Such type I domains carrying 4, or occasionally 6 or more, cysteine residues have been previously encountered. The ability to form these additional disulphide bonds, combined with the small size of the NAR V region, may provide an additional source for highly stable antibody fragments.

Colonies, which were not sequenced, were scraped from the library plates with a sterile spreader into a final volume of 10 ml 2×TY medium containing 100 μg/ml ampicillin and 2% glucose. Cells were combined with sterile glycerol to 20% (v/v), and following thorough mixing aliquotted as 500 μl shots and flash-frozen prior to storage at −80° C.

Panning of NAR V Region Library Against Protein Antigens Growth of the Library

A single aliquot of library stock was added to 200 ml of pre-warmed 2×TY medium containing ampicillin at 100 μg/ml and 1-2% glucose (w/v) and grown at 37° C./250 rpm until log phase (OD$_{600}$ of 0.4-0.8) was reached. To a 50 ml sample taken from the culture approximately $10^{15}$ of M13K07 helper phage were added and the culture incubated at 37° C. without shaking to allow infection. Following incubation the culture was spun at 3.5K rpm/4° C. for 10 min and the cell pellet re-suspended in 100 ml of 2×TY containing 100 μg/ml ampicillin, 50 μg/ml kanamycin and 0.1-0.25% glucose and incubated overnight at 30° C./250 rpm to allow library expression and rescue.

The overnight culture was spun at 12K rpm/4° C. for 20 min, 80 ml of supernatant was removed and added to 20 ml of PEG/NaCl, mixed well and incubated on ice for at least 1 h. The precipitated phage was pelleted at 12K rpm/4° C. and re-suspended in 2 ml PBS. The phage suspension was spun at 13K rpm for 10 min to remove any remaining bacterial debris and the phage supernatant stored at 4° C. The phage stock was titrated by performing serial dilutions in PBS and the addition of 900 µl of a log phase culture to 100 µl of each dilution. Following incubation at 37° C. for 30 min, 100 µl of each dilution was plated on TYE plates containing ampicillin at 100 µg/ml and 1% glucose and incubated overnight at 37° C. The phage titre could be estimated by counting the resulting colonies.

Library Selection

Nunc MAXISORP IMMUNO test tubes (Gibco BRL, Life technologies Ltd.) were coated with either HEL or Ova in 4 ml of PBS overnight at 4° C. The tube was then washed 3 times with PBS before being blocked with 2% Marvel in PBS (MPBS) for 2 h at room temperature, following which it was washed a further 3 times with PBS. Selection was conducted by incubating the coated immunotube for 1 h at room temperature with 1 ml of phage stock in 3 ml of 2% MPBS on an over-and-under tumbler. A further hour of stationary incubation was allowed before the supernatant containing unbound phage was discarded and bound phage eluted as described below.

Elution and Rescue of Antigen-Bound Phage

Triethylamine Elution

Binding individuals of the antigen specific antigen binding domain library, displayed on the phage strain M13K07, were eluted using the alkali triethylamine.

Following incubation with phage the immunotube was washed 20 times with PBST, excess liquid drained off and 1 ml of 100 mM triethylamine added. The tube was then rotated for a maximum of 10 min at room temperature to elute bound phage. Following incubation the phage solution was neutralized by mixing with 500 µl of 1 M Tris-HCl. In this state the phage solution was stored at 4° C. for further use (or long-term at −20° C. if glycerol added at 15% v/v).

To 750 µl of the triethylamine-eluted phage 10 ml of a log phase bacterial culture was added and the culture incubated at 37° C. without shaking for 30 min. Serial dilutions of the culture were prepared in 2×TY and plated on TYE plates containing 100 µg/ml ampicillin and 2% glucose to allow the number of rescued phage to be estimated. The remaining infected culture was spun for 10 min at 13K rpm, re-suspended in 100 µl of 2×TY and plated on a 140 mm petri-dish containing TYE as above. Plates were grown overnight at 37° C.

Rescue of Selected Phage

After overnight growth, colonies were scraped from the large petri-dishes into 2 ml of 2×TY medium with a sterile scraper and the suspension mixed thoroughly. Following inoculation of 50 ml 2×TY containing 100 µg/ml ampicillin and 1-2% glucose with 50 µl of this suspension, 1 ml of the remaining bacteria was mixed with 15% glycerol (v/v) and stored at −80° C. as a stock. The 50 ml culture was incubated at 37° C./250 rpm until the $OD_{600}$ reached 0.4, whereupon 15 ml was removed, added to approximately $10^{10}$ helper phage and incubated for 30 min at 37° C. Following incubation the culture was spun at 3.5 K rpm for 10 min and the resultant cell pellet re-suspended in 2×TY containing 100 µg/ml ampicillin, 50 µg/ml kanamycin and 0.1-0.25% glucose and incubated overnight at 30° C./250 rpm.

The overnight culture was spun at 12K rpm for 10 min and 40 ml of supernatant added to 10 ml of PEG/NaCl, and mixed well prior to incubation on ice for at least 1 h. The phage pellet was again re-suspended in 2 ml of PBS and spun for 10 min at 13K rpm to remove any remaining bacterial debris and the phage stored at 4° C. for the short term.

Further rounds of selection were carried out with phage rescued from the previous round of selection, as above, on antigen coated immunotubes.

The immune library was subject to five rounds of panning against the protein antigens Hen egg white lysozyme (HEL) and Chicken ovalbumin (Ova), independently, using M13K07 helper phage and triethylamine elution. A summary of the panning results are given in Table 1.

In an attempt to minimize loss of clone diversity in early rounds of selection the antigen coating density was kept constant at 100 µg/ml for pans 1 and 2. Following the first round of panning approximately $10^6$ phage were eluted from both the HEL and Ova coated immunotubes, increasing 10-fold following pan 2. For pans 3 and 4 the antigen coating density was reduced for each pan in an attempt to select higher affinity binders. Whilst the number of phage eluted following HEL selection remained constant at ~$10^6$ for both pans that for Ova selection dropped to $10^3$ in pan 3, rising back to $10^6$ following pan 4. For pan 5 the antigen coating concentration was further reduced and selection was accompanied by a significant drop in the number of phage eluted. Due to this reduction in the number of phage eluted polyclonal and monoclonal phage ELISAs were conducted to determine if enrichment of HEL or Ova binders was occurring (FIG. 5).

The binding of the HEL-selected polyclonal phage showed a small increase in $OD_{450}$ over pans 1 and 2, with a significant increase following pan 3. A further small increase in signal followed pan 4, but afterwards pan 5 dropped back to the level observed for earlier pans. A similar pattern was observed for the Ova-selected polyclonal phage with the highest binding being obtained for phage rescued after pan 4, however in this instance the $OD_{450}$ values remain low (below 0.25) for all pans.

Monoclonal phage ELISAs show an increase in the number of positive phage for both sets of selection over pans 1 to 4. In the case of HEL selection this increase was from less than 1% to approximately ~80% following pan 4. For Ova selected clones the numbers of positives was slightly lower but regardless increased from less than 1% to approximately 66% after the fourth pan. Following pan 5 the number of HEL-positive clones remained constant at 80% but the number of Ova-positive monoclonals dropped back to the levels observed in earlier pans (~10%).

The drop in the number of clones able to bind Ova after pan 5 indicates that for this pan the protein coating concentration has been reduced such that the selection is too stringent and the majority of clones are no longer able to bind. No such drop is observed for the HEL-selected monoclonal assay, indicating that the affinity of these clones for their antigen is probably higher. This shows that the antigen specific antigen binding domains produced by the sharks are very specific as the sharks were immunised with HEL and only HEL binders could be isolated, Ova data shows no binders. For this reason a selection of clones from pans 3 and 4 were sequenced for Ova but from pans 4 and 5 for HEL.

TABLE 1

| Pan | phage added (φ/ml) | coating density µg/ml | phage eluted (φ/ml) |
|---|---|---|---|
| Anti-Hel selection | | | |
| 1 | >$10^{12}$ | 100 | 105 |
| 2 | >$10^{12}$ | 100 | 106 |
| 3 | >$10^{12}$ | 50 | 106 |
| 4 | >$10^{12}$ | 1 | 106 |
| 5 | >$10^{12}$ | 0.1 | 103 |

TABLE 1-continued

| Pan | phage added (φ/ml) | coating density µg/ml | phage eluted (φ/ml) |
|---|---|---|---|
| Anti-Ova selection | | | |
| 1 | >10$^{12}$ | 100 | 10$^5$ |
| 2 | >10$^{12}$ | 100 | 10$^6$ |
| 3 | >10$^{12}$ | 50 | 10$^3$ |
| 4 | >10$^{12}$ | 1 | 10$^5$ |
| 5 | >10$^{12}$ | 0.1 | 10$^3$ |

Selection Analysis
Polyclonal Phage ELISA

A 96-well IMMULON 4 ELISA plate (Dynatech Laboratories Ltd.) was coated with 100 µl of antigen at 10 µg/ml for 1 h at 37° C. Following three washes with PBST the wells were blocked with 300 µl of 2% MPBS (PBS with 2% w/v marvel added) for a further hour at room temperature of overnight at 4° C. Wells were washed 3 times with PBST and to individual wells 10 µl of PEG precipitated phage from each pan, in 100 µl of 2% MPBS, was added and the plate incubated for 1 h at room temperature. The phage solution was discarded and the plate washed with PBST 3 times. To each well 100 µl of anti-M13 monoclonal HRP conjugate (APB Ltd.), diluted 1 in 5000 in PBS, was added and incubated at room temperature for 1 h. The plate was washed 5 times with PBST and developed with 100 µl per well of TMB substrate, the reaction stopped with 50 µl per well of 1 M $H_2SO_4$ and the plate read at 450 nm.

Monoclonal Phage ELISA

Individual colonies growing on TYE plates were picked into 100 µl 2×TY medium containing 100 µg/ml ampicillin and 1-2% glucose on a sterile 96-well ELISA plate, for each of the pans, and grown overnight at 37° C./250 rpm. Following growth, a 96-well transfer device was used to inoculate a fresh 96-well plate containing 200 µl per well of 2×TY with 100 µg/ml ampicillin and 1-2% glucose. Bacteria were grown for 2 h at 37° C./250 rpm. To the original overnight plate glycerol was added to give a final concentration of 15% and the plates stored at −80° C. as a bacterial stock.

After the two hour incubation 25 µl of 2×TY containing 100 µg/ml ampicillin, 1-2% glucose and 10$^{10}$ helper phage were added to each well. The plate was then incubated for a further hour at 37° C./250 rpm before being spun at 2K rpm for 10 min to pellet the bacteria. Supernatant was aspirated from the plate and the resultant pellet re-suspended in 200 µl 2×TY containing 100 µg/ml ampicillin, 50 µg/ml kanamycin and glucose at 0.25% (w/v). The plate was then incubated overnight at 30° C./250 rpm.

The overnight plate was spun at 2K rpm for 10 min to give a supernatant containing monoclonal phage supernatant. To suitably coated and blocked plates, 50 µl of this phage supernatant in 50 µl of MPBS was added per well and the plate incubated at room temperature for 1 h. Following incubation the plate was incubated with anti-M13 HRP conjugated antibody and developed as normal.

Subcloning and Sequencing of Positive Monoclonal Phage Clones

Following determination of individual clones giving a positive signal for antigen binding, 5 ml of 2×TY containing 2% glucose and 100 µg/ml ampicillin was inoculated from the appropriate clone source. Taking into account the results of the monoclonal phage ELISAs fifteen HEL-positive clones were picked at random from pans 4 and 5, whilst those for Ova were picked from pans 3 and 4. Following overnight incubation of the cultures at 37° C./250 rpm plasmid was prepared as set out above. A 20 µl sample of plasmid was then digested with the restriction enzymes NcoI and NotI and the ~400 bp fragment corresponding to the NAR V region fragment PAGE purified and recovered. Purified V region fragments were then ligated into similarly cut, alkaline phosphatase treated and cleaned pIMS100 expression vector. Following overnight incubation at 15° C. the resultant vector, harbouring the NAR V insert fused upstream of the HuCk domain and 6His tail, was transformed into electroporation-competent E. coli XL1-Blue cells. Colonies were picked, grown as overnight cultures in 5 ml TB (containing 2% glucose (v/v), 100 µg/ml ampicillin, 25 µg/ml tetracycline) and glycerol stocks and plasmid prepared.

Inserts were sequenced from plasmid using the M13 reverse (5' TTCACACAGGAAACAG 3') (SEQ ID. 67) and HuCk forward (5' GAAGATGAAGACAGATGGTGC 3') (SEQ ID. 68) primer. Once sequence data had been generated the clone was given a unique name to enable identification.

On translation only two different sequences were obtained from the 15 HEL-selected clones and two from the 15 Ova-selected clones.

The clones 5A7 and 4F11 were chosen to represent the two different amino acid sequences found within the HEL-selected positive clones (FIGS. 6 and 7). The two clones are both conventional NAR type I, and so are illustrated aligned against a typical type I clone in FIG. 8. The two clones differ from one another at only two positions (43 & 44), both lying within Fr2 and carry identical CDR3 regions.

The clones 4H11 and 3E4 were chosen to represent the two different amino acid sequences found within the Ova-selected positive clones (FIGS. 9 and 10). Again these clones were both conventional NAR type I and as such are shown aligned against a typical type I clone in FIG. 11. These clones differ at 6 amino acids; three within Fr1 (positions 13, 14 & 30), two within Fr2 (positions 46 & 47) and one within CDR3 (position 101).

Expression of Antigen Binding Domains in E. coli Large Scale Expression

A single colony of transformed E. coli was used to inoculate 5 ml LB containing 1% glucose (v/v), 12.5 µg/ml tetracycline and 50 µg/ml ampicillin and grown up at 37° C./250 rpm overnight. This culture was used to seed 50 ml TB medium containing 1% glucose (v/v), 12.5 µg/ml tetracycline and 50 µg/ml ampicillin in 250 ml baffled flasks, at 1% v/v. The 50 ml cultures were grown over a period of 24 hours at 25° C./250 rpm, with one change of media after approximately 10 hours growth. Growth of all the cultures was good with the overnight $OD_{600}$ being in the order of 10-20 OD units.

Overnight cultures were pelleted at 4 K rpm/4° C. for 20 min. Pellets were resuspended in 50 ml fresh TB containing 50 µg/ml ampicillin and given 1 h at 25° C./250 rpm to recover before induction with 1.5 mM IPTG for 3.5-4 h and release of periplasmic contents.

Periplasmic Burst Release Method

The cell pellet resulting from centrifugation was resuspended in 10% of the original culture volume of fractionation buffer (100 ml 200 mM Tris-HCl, 20% sucrose, pH 7.5, 1 ml 100 mM EDTA/L of culture). The suspension was incubated on ice with gentle shaking for 15 min following which an equal volume of ice-cold sterile $H_2O$ was added and incubation continued for a further 15 min (method modified from French et al., Enzyme & Microbial Technology 19 pp 332-338 1996). The suspension was spun at 13K rpm/4° C. for 20 min, the supernatant containing the periplasmic fraction harvested and passed through a 0.22 µm filter (Sartorius Instruments Ltd.).

None of the cultures showed any sign of bacterial lysis during the 4 h induction period and expression yields in the order of 1 mg crude NAR protein per liter of culture were obtained. In this example the protein expressed from the four selected clones was IMAC purified via the 6H is tail.

ELISA Analysis of Antigen Binding Domains

Antigen Binding ELISA

An IMMULON 4 96-well flat bottomed ELISA plate was coated with a suitable concentration of the desired antigen at 100 yl per well and the plate incubated at 37° C. for 1 h. The plate was washed 3 times with PBST prior to blocking with 200 μl per well of PBS containing 2% Marvel (w/v) for 1 h at 37° C. Wells were washed a further three times with PBST before addition of samples.

A 1 in 5 dilution of crude periplasmic release solution was prepared, added to the top wells of the plate at 200 μl per well and doubling dilutions in PBS performed. Plates were then incubated at 4° C. for 1 h. Each plate was washed a further 5 times with PBST. Goat anti-HuCk peroxidase conjugate antibody was diluted 1:1000 in PBS and 100 μl added to wells containing antigen binding domains. Plates were incubated for 1 h at 4° C. and following 6 washes with PBST the ELISA was developed as described previously and the plate read at 450 nm.

The HEL-selected clone 5A7 (FIG. 12) shows good binding to HEL at the top dilution applied and as the sample is serially diluted binding reduces accordingly. Limited binding to the highly related protein turkey egg-white lysozyme (TEL) is observed at the highest dilution but no binding is observed to the proteins Chicken ovalbumin (Ova), Bovine serum albumin (BSA), Keyhole limpet haemocyanin (KLH) or the blocking agent Marvel. An identical pattern of protein binding is also observed for the HEL-selected clone 4F11 (FIG. 13), which is not surprising considering the high degree of amino acid sequence similarity between these two clones (111/113 aa identical). The $OD_{450}$ signals obtained for 3F11 are slightly higher than those for 5A7, but this may simply be due to small differences in the amount of protein present in the samples.

The Ova-selected clone 4H11 (FIG. 14) showed no binding to any of the proteins tested, including Ova, the antigen it was selected against. To ensure that this was not simply a consequence of there being too little protein present in the assay, a binding assay was performed with undiluted periplasmic release solution. In this instance some binding to all of the proteins was observed for the wells containing the top dilutions of 4H11 protein. This binding was immediately lost once the sample was diluted and so is likely to be non-specific, no doubt resulting from very high concentrations of protein being present. This data supported the initial finding that the 4H11 clone does not bind significantly to Ova. The 3E4 clone, like 4H11, does not show binding to the proteins HEL, BSA, KLH, TEL or the blocking agent. Marvel, however low level binding is observed for this clone to the selection antigen Ova. The pattern of binding by this clone to Ova is unusual in that binding at the highest protein concentration is low and shows no significant drop on dilution of the sample. When the protein concentration was increased by repeating the assay with undiluted periplasmic solution a similar pattern of binding was observed, thus negating the possibility that the protein concentration was initially too low. The reason for this unusual binding is as yet unknown, but may be due to 3E4 binding only with low affinity to Ova.

The distinct lack of NAR clones capable of binding antigen in a library previously constructed from material from a naïve animal and the isolation of HEL-binding, but not Ova-binding clones, from the library constructed from the HEL immunised animals illustrates the highly specific nature of the NAR response following antigen challenge. In other words, antigen specific antigen binding domains with a specific specificity are produced.

Stability Analysis of Selected Clones

As clones 5A7 and 4F11 were shown to be capable of binding HEL in the antigen binding ELISA it was possible to test the stability of these clones to thermal denaturation. Sub-saturating dilutions of both of the clones, ascertained from the antigen binding curves, were prepared and incubated at a range of temperatures for 3 h prior to their addition to a HEL coated ELISA plate. The samples were then incubated on the ELISA plate for an hour at 4° C. and binding detected with an anti-HuCk HRP conjugated antibody. Stability of the antigen binding domains was plotted as a percentage of that obtained for a control sample which had not been heat treated (FIG. 15).

Both clone 5A7 and clone 4F11 show considerable resistance to irreversible denaturation losing 50% functionality at approximately 85° C. and retaining approximately 30% functionality after 3 h at 95° C. This high stability is probably a consequence of the additional, non-canonical cysteine residues found within the NAR V domain. Both clones encode 6 cysteine residues and therefore are capable of forming 3 intradomain disulphide bonds, which (if formed) would contribute greatly to the high stability of these domains. The shape of the stability curves for both of the clones is almost identical and the minor difference in stability between the clones may be simply due to assay variability.

Repetition of this assay utilising an anti-His HRP conjugated antibody to detect binding generated values which were not significantly different to those obtained with the anti-HuCk secondary antibody, indicating the drop in signal is caused by reduced binding of the NAR V domains, due to denaturation, and not simply reduced detection via the HuCk tag.

Inhibition of Protein Activity

The ability of HEL-5A7 to inhibit the enzymatic activity of HEL was tested by mixing 12.5 μl of HEL with 12.5 μl of purified HEL-5A7 protein in a sterile 96 well tissue culture plate, to give a final HEL concentration of 10 μg/ml and HEL-5A7 concentrations of 2500 nM, 250 nM and 25 nM. The control well was set up with buffer replacing HEL-5A7. A sample of freeze dried *Micrococcus lysodeikticus* was reconstituted in 0.1 M phosphate/citrate buffer (pH 5.8) containing 0.09% NaCl, mixed thoroughly and 175 μl added to the prepared wells. The plate was read over a period of 30 min (at 1 min intervals) at 450 nm. Enzymatic activity was plotted as percentage initial absorbance against time for each sample.

The introduction of HEL-5A7 protein to the assay reduced the rate of cell lysis in a concentration dependent manner with respect to the control (FIG. 16). With HEL-5A7 protein at a final concentration of 2500 nM the rate of cell lysis ($9.3 \times 10^{-3}$ OD units/min) is almost halved when compared to the control ($17 \times 10^{-3}$ OD units/min) indicating that the HEL-5A7 region binds within or adjacent to the lysozyme active site cavity. A similarly prepared antigen specific antigen binding domain raised against an unrelated antigen showed no effect upon the rate of cell lysis when introduced to the assay at the same concentrations.

It will be understood that the embodiment illustrated shows one application of the invention only for the purposes of illustration. In practice the invention may be applied to many different configurations, the detailed embodiments being straightforward for those skilled in the art to implement.

SEQUENCE LISTING

<160> NUMBER OF SEQ ID NOS: 70

<210> SEQ ID NO 1
<211> LENGTH: 116
<212> TYPE: PRT
<213> ORGANISM: Ginglymostoma cirratum

<400> SEQUENCE: 1

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Gly Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Ser Pro Trp Gly Trp Gly Arg Ser Cys Asp Tyr
                85                  90                  95

Pro Ser Cys Ala Gln Arg Pro Tyr Ala Ala Cys Gly Asp Gly Thr Ala
            100                 105                 110

Val Thr Val Asn
        115

<210> SEQ ID NO 2
<211> LENGTH: 114
<212> TYPE: PRT
<213> ORGANISM: Ginglymostoma cirratum

<400> SEQUENCE: 2

Ala Arg Val Asp Gln Thr Pro Gln Glu Ile Thr Lys Glu Thr Gly Glu
1               5                   10                  15

Ser Leu Ser Ile Asn Cys Val Leu Arg Asp Asp Ser Cys Ala Leu Pro
            20                  25                  30

Ser Thr Tyr Trp Asn Arg Lys Lys Ser Gly Ser Thr Asn Glu Glu Thr
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Tyr Arg Lys Asn Trp Ala Tyr Asp Cys Gly Leu
                85                  90                  95

Glu Glu Leu Asp Trp Ile Tyr Val Tyr Gly Gly Gly Thr Val Val Thr
            100                 105                 110

Val Asn

<210> SEQ ID NO 3
<211> LENGTH: 115
<212> TYPE: PRT
<213> ORGANISM: Ginglymostoma cirratum

<400> SEQUENCE: 3

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

```
Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Ser Thr Trp Cys Arg Thr Cys Cys Asp Tyr Glu
                85                  90                  95

Thr Gly Leu Cys Ser Ala Tyr Ala Ala Cys Gly Asp Gly Thr Ala Val
            100                 105                 110

Thr Val Asn
    115

<210> SEQ ID NO 4
<211> LENGTH: 109
<212> TYPE: PRT
<213> ORGANISM: Ginglymostoma cirratum

<400> SEQUENCE: 4

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Gly Ser Trp Glu Pro Val Thr Gly Cys Ala Val Asn
                85                  90                  95

Tyr Ala Ala Cys Gly Asp Gly Thr Ala Val Thr Val Asn
            100                 105

<210> SEQ ID NO 5
<211> LENGTH: 127
<212> TYPE: PRT
<213> ORGANISM: Ginglymostoma cirratum

<400> SEQUENCE: 5

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Asn Tyr Ala Leu Gly
            20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Cys Thr Val Met Ser Leu Ile Phe His Leu Asp
                85                  90                  95

Arg Ile Leu Ser Asn Leu Leu Ser Asn Thr Asp Asp Leu Ile Asp Cys
            100                 105                 110

Asp Asn Tyr Ala Ala Cys Gly Asp Gly Thr Ala Val Thr Val Asn
    115                 120                 125
```

```
<210> SEQ ID NO 6
<211> LENGTH: 111
<212> TYPE: PRT
<213> ORGANISM: Ginglymostoma cirratum

<400> SEQUENCE: 6

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Thr Val Glu Asp Gly Gly Thr
 65                  70                  75                  80

Tyr Arg Cys Gly Glu Pro Leu Val Trp Ser Glu Leu His Ala Cys Ser
                 85                  90                  95

Ser Pro Tyr Ala Ala Cys Gly Asp Gly Thr Ala Val Thr Val Asn
            100                 105                 110

<210> SEQ ID NO 7
<211> LENGTH: 112
<212> TYPE: PRT
<213> ORGANISM: Ginglymostoma cirratum

<400> SEQUENCE: 7

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Thr Val Glu Asp Gly Gly Thr
 65                  70                  75                  80

Tyr Arg Cys Gly Leu Asn Pro Thr Leu Leu Leu Cys Ser Cys Gly
                 85                  90                  95

Ser Ser Ile Tyr Ala Ala Cys Gly Asp Gly Thr Ala Val Thr Val Asn
            100                 105                 110

<210> SEQ ID NO 8
<211> LENGTH: 114
<212> TYPE: PRT
<213> ORGANISM: Ginglymostoma cirratum

<400> SEQUENCE: 8

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Thr Val Ile Asp Gly Gly Thr
```

```
                65                  70                  75                  80
Tyr Arg Cys Gly Leu Gln Leu Val Trp Ile Pro Pro Leu Leu Arg Leu
                    85                  90                  95

Gly Gly Ala Leu Pro Tyr Gly Ala Cys Gly Glu Gly Thr Ala Val Thr
                100                 105                 110

Val Asn

<210> SEQ ID NO 9
<211> LENGTH: 103
<212> TYPE: PRT
<213> ORGANISM: Ginglymostoma cirratum

<400> SEQUENCE: 9

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Asn Cys Val Phe Ser
            20                  25                  30

Arg Thr Tyr Trp Tyr Arg Lys Lys Ser Gly Ser Thr Asn Glu Glu Asn
        35                  40                  45

Ile Ser Lys Gly Gly Arg Trp Ser Ile Cys Asn Asn Pro His Gln Arg
    50                  55                  60

Ile Lys Val Leu Phe Phe Gly Asn Gly Ser Met Ser Arg Lys Cys His
65                  70                  75                  80

Val Ser Met Arg Gly Arg Tyr Thr Pro Glu Asp Asn Asn Leu Gly Asp
                85                  90                  95

Gly Thr Ala Val Thr Val Asn
            100

<210> SEQ ID NO 10
<211> LENGTH: 111
<212> TYPE: PRT
<213> ORGANISM: Ginglymostoma cirratum

<400> SEQUENCE: 10

Ala Arg Val Asp Gln Thr Pro Gln Ser Val Thr Lys Glu Thr Gly Glu
1               5                   10                  15

Ser Leu Thr Ile Asn Cys Val Leu Arg Thr Glu Thr Tyr Ser Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Pro Gly Ile Ala Gly Gly Ser Gly Cys Ala Leu
                85                  90                  95

Leu Thr Leu Cys Cys Met Arg Arg Trp His Cys Arg Thr Val Asn
                100                 105                 110

<210> SEQ ID NO 11
<211> LENGTH: 105
<212> TYPE: PRT
<213> ORGANISM: Ginglymostoma cirratum

<400> SEQUENCE: 11

Ala Arg Val Asp Gln Thr Pro Arg Ser Val Thr Lys Glu Thr Gly Glu
1               5                   10                  15
```

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Trp Trp Glu Leu Leu Arg Gly Ala Leu Tyr Met
                85                  90                  95

Leu His Ala Asp Met Ala Leu Pro Leu
            100                 105

<210> SEQ ID NO 12
<211> LENGTH: 116
<212> TYPE: PRT
<213> ORGANISM: Ginglymostoma cirratum

<400> SEQUENCE: 12

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Trp Ile Ala Gly Val Asp Tyr Asp Tyr Ser Leu
                85                  90                  95

Ala Val Leu Leu Ser Ser Thr Ser Met Ala Met Leu His Ala Glu Met
            100                 105                 110

Ala Leu Pro Leu
        115

<210> SEQ ID NO 13
<211> LENGTH: 105
<212> TYPE: PRT
<213> ORGANISM: Ginglymostoma cirratum

<400> SEQUENCE: 13

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Glu Ala His Pro Leu Arg Ser Ser Val Thr Thr Met
                85                  90                  95

Leu His Ala Glu Met Ala Leu Pro Leu
            100                 105

<210> SEQ ID NO 14
<211> LENGTH: 114
<212> TYPE: PRT
<213> ORGANISM: Ginglymostoma cirratum

<400> SEQUENCE: 14

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Gly Gly Thr
65                  70                  75                  80

Tyr Arg Cys Gly Val Val Phe Leu Ala Asp Ser Trp Cys Gly Ser Val
                85                  90                  95

Val Thr Ser Cys Ala Leu Pro Pro Met Leu His Ala Glu Met Ala Leu
            100                 105                 110

Pro Leu

<210> SEQ ID NO 15
<211> LENGTH: 104
<212> TYPE: PRT
<213> ORGANISM: Ginglymostoma cirratum

<400> SEQUENCE: 15

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Gly Gly Thr
65                  70                  75                  80

Tyr Arg Cys Gly Ile Trp Arg Cys Ser Cys Leu Cys Gly Cys Met Leu
                85                  90                  95

His Ala Glu Met Ala Leu Pro Leu
            100

<210> SEQ ID NO 16
<211> LENGTH: 109
<212> TYPE: PRT
<213> ORGANISM: Ginglymostoma cirratum

<400> SEQUENCE: 16

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
50                  55                  60

```
Ser Phe Ser Leu Arg Ile Asn Asp Leu Thr Val Glu Asp Gly Gly Thr
 65                  70                  75                  80

Leu Arg Cys Gly Ile Met Val Cys Cys Asp Ser Phe Gly Ser Val Leu
                 85                  90                  95

Tyr Arg Arg Glu Leu His Ala Glu Met Ala Leu Pro Leu
            100                 105
```

<210> SEQ ID NO 17
<211> LENGTH: 112
<212> TYPE: PRT
<213> ORGANISM: Ginglymostoma cirratum

<400> SEQUENCE: 17

```
Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
         50                  55                  60

Ser Phe Ser Leu Arg Ile Asn Asp Leu Thr Val Glu Asp Gly Gly Thr
 65                  70                  75                  80

Tyr Arg Cys Gly Val Cys Arg Thr Trp Gly Ser Arg Cys Asp Leu Ala
                 85                  90                  95

His Val Leu Leu Gly Cys Met Arg Arg Trp His Cys Arg Asp Cys Glu
            100                 105                 110
```

<210> SEQ ID NO 18
<211> LENGTH: 105
<212> TYPE: PRT
<213> ORGANISM: Ginglymostoma cirratum

<400> SEQUENCE: 18

```
Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
         50                  55                  60

Ser Phe Ser Leu Arg Ile Asn Asp Leu Thr Val Glu Asp Gly Gly Thr
 65                  70                  75                  80

Tyr Arg Cys Gly Ala Gly Ile Leu Val Glu Gly Ser Arg Gly Cys Met
                 85                  90                  95

Arg Arg Trp His Cys Arg Asp Cys Glu
            100                 105
```

<210> SEQ ID NO 19
<211> LENGTH: 108
<212> TYPE: PRT
<213> ORGANISM: Ginglymostoma cirratum

<400> SEQUENCE: 19

```
Ala Arg Val Asp Gln Thr Pro Arg Ser Val Thr Lys Glu Thr Gly Glu
 1               5                  10                  15
```

```
Ser Leu Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Thr Val Glu Asp Gly Gly Thr
 65              70                  75                      80

Tyr Arg Cys Gly Val Arg Arg Ile Leu Val Trp Met Leu Leu Thr Val
             85                  90                  95

Cys Cys Met Arg Arg Trp His Cys Arg Asp Cys Glu
            100                 105
```

<210> SEQ ID NO 20
<211> LENGTH: 109
<212> TYPE: PRT
<213> ORGANISM: Ginglymostoma cirratum

<400> SEQUENCE: 20

```
Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Thr Val Glu Asp Gly Gly Thr
 65              70                  75                      80

Tyr Arg Cys Gly Val Gly Val Trp Ile Cys Asp Glu Thr Leu Ser Cys
             85                  90                  95

Ala Leu Asp Arg Ala Ala Cys Gly Asp Gly Thr Ala Leu
            100                 105
```

<210> SEQ ID NO 21
<211> LENGTH: 108
<212> TYPE: PRT
<213> ORGANISM: Ginglymostoma cirratum

<400> SEQUENCE: 21

```
Ala Arg Val Asp Gln Thr Pro Lys Thr Ile Thr Lys Glu Thr Gly Glu
 1               5                  10                  15

Ser Leu Thr Ile Asn Cys Val Leu Ser Asp Thr Ser Cys Ala Trp Asp
             20                  25                  30

Ser Thr Tyr Trp Tyr Arg Lys Lys Leu Asp Ser Thr Asn Glu Glu Ser
         35                  40                  45

Thr Ser Lys Gly Gly Arg Tyr Val Glu Thr Val Asn Ser Glu Ser Thr
     50                  55                  60

Ser Phe Ser Leu Arg Ile Asn Asp Leu Thr Val Glu Asp Ser Gly Thr
 65              70                  75                      80

Tyr Arg Cys Arg Ala Tyr Pro Gly Leu Leu Tyr Cys Gly Tyr His Gly
             85                  90                  95

Ala Leu Ile Trp Arg Trp His Cys Arg Asp Cys Glu
            100                 105
```

<210> SEQ ID NO 22
<211> LENGTH: 102

```
<212> TYPE: PRT
<213> ORGANISM: Ginglymostoma cirratum

<400> SEQUENCE: 22

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Gly Tyr Ile Gly Gly Leu Gly Val Met Tyr Thr
                85                  90                  95

Glu Val Ala Leu Ser Leu
                100

<210> SEQ ID NO 23
<211> LENGTH: 111
<212> TYPE: PRT
<213> ORGANISM: Ginglymostoma cirratum

<400> SEQUENCE: 23

Ala Arg Val Asp Gln Thr Pro Gln Thr Ile Thr Lys Glu Thr Gly Glu
 1               5                  10                  15

Ser Leu Thr Ile Tyr Cys Val Leu Gln Asp Ser Ile Cys Gly Leu Ser
            20                  25                  30

Ser Thr Tyr Trp Tyr Arg Lys Arg Ser Gly Ser Pro Asn Glu Leu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Gly Leu Thr Val Leu Asp Ser Ala Gly
65                  70                  75                  80

Gly Thr Pro Leu Cys Lys Leu Val Pro Asn Gln Leu Ala Pro Asp Leu
                85                  90                  95

Thr Phe Arg Thr Thr Leu Met Tyr Thr Glu Met Ala Leu Pro Leu
                100                 105                 110

<210> SEQ ID NO 24
<211> LENGTH: 108
<212> TYPE: PRT
<213> ORGANISM: Ginglymostoma cirratum

<400> SEQUENCE: 24

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ile Gly Leu Asn Lys Arg Gly Glu
        35                  40                  45

His Ile Glu Arg Trp Thr Ile Cys Asn Ser Gln Arg Ile Lys Val Val
    50                  55                  60

Leu Phe Phe Glu Asn Ser Asn Ser Arg Arg Trp His Val Ser Leu Arg
65                  70                  75                  80

Cys Leu Asp Arg Leu Gly Ala Val Thr Thr Tyr Arg Cys Ala Leu Pro
```

```
                85                  90                  95

Arg Gly Met Leu His Ala Glu Met Ala Leu Pro Leu
            100                 105

<210> SEQ ID NO 25
<211> LENGTH: 109
<212> TYPE: PRT
<213> ORGANISM: Ginglymostoma cirratum

<400> SEQUENCE: 25

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Trp Gly Gln Leu His Val Arg Cys Ala Leu Gly
                85                  90                  95

Asp Ala Ala Cys Gly Asp Gly Thr Ala Val Thr Val Asn
            100                 105

<210> SEQ ID NO 26
<211> LENGTH: 113
<212> TYPE: PRT
<213> ORGANISM: Ginglymostoma cirratum

<400> SEQUENCE: 26

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Pro Asp Ser Trp Trp Arg Phe Ala Val Val Cys
                85                  90                  95

Ala Leu Glu Pro Asp Ala Ala Cys Gly Asp Gly Thr Ala Val Thr Val
            100                 105                 110

Asn

<210> SEQ ID NO 27
<211> LENGTH: 111
<212> TYPE: PRT
<213> ORGANISM: Ginglymostoma cirratum

<400> SEQUENCE: 27

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30
```

```
Ser Thr Tyr Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
 65                  70                  75                  80

Tyr Arg Cys Gly Val Cys Pro His Phe Ser Trp Cys Arg Leu His Glu
             85                  90                  95

Gln Cys Ala Leu Ala Gly Gly Asp Gly Thr Ala Val Thr Val Asn
            100                 105                 110
```

<210> SEQ ID NO 28
<211> LENGTH: 117
<212> TYPE: PRT
<213> ORGANISM: Ginglymostoma cirratum

<400> SEQUENCE: 28

```
Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
 50                  55                  60

Ser Phe Ser Leu Arg Ile Asn His Leu Thr Val Glu Asp Gly Gly Thr
 65                  70                  75                  80

Tyr Arg Cys Gly Val Cys Asp Ser Ser Ile Ala Val Ala Gly Cys
             85                  90                  95

Gly Tyr Cys Leu Cys Thr Leu Val His Ser Val Cys Gly Asp Gly Thr
            100                 105                 110

Ala Val Thr Val Asn
        115
```

<210> SEQ ID NO 29
<211> LENGTH: 109
<212> TYPE: PRT
<213> ORGANISM: Ginglymostoma cirratum

<400> SEQUENCE: 29

```
Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
 65                  70                  75                  80

Tyr Arg Cys Gly Ala Arg Ala Gly Gly Pro Phe Leu Cys Ser Cys Val
             85                  90                  95

Tyr Ala Ala Cys Gly Asp Gly Thr Ala Val Thr Val Asn
            100                 105
```

<210> SEQ ID NO 30
<211> LENGTH: 115

```
<212> TYPE: PRT
<213> ORGANISM: Ginglymostoma cirratum

<400> SEQUENCE: 30

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Pro Val Gly Arg Ser Cys Asp Tyr Pro Gln Leu
                85                  90                  95

Cys Ser Trp Gly Leu Asn Tyr Ala Ala Cys Gly Asp Gly Thr Ala Val
            100                 105                 110

Thr Val Asn
        115

<210> SEQ ID NO 31
<211> LENGTH: 113
<212> TYPE: PRT
<213> ORGANISM: Ginglymostoma cirratum

<400> SEQUENCE: 31

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Gly Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Ser Thr Ala Gly Val Asp Cys Asp Tyr Thr Cys
                85                  90                  95

Ala Leu Trp Asp Tyr Ala Ala Cys Gly Asp Gly Thr Ala Val Thr Val
            100                 105                 110

Asn

<210> SEQ ID NO 32
<211> LENGTH: 117
<212> TYPE: PRT
<213> ORGANISM: Ginglymostoma cirratum

<400> SEQUENCE: 32

Ala Arg Val Asp Gln Thr Pro Arg Ser Val Thr Lys Glu Ala Gly Glu
 1               5                  10                  15

Ser Leu Ala Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60
```

-continued

```
Ser Phe Ser Leu Arg Ile Asn Asp Leu Thr Val Glu Asp Gly Gly Thr
 65                  70                  75                  80

Tyr Arg Cys Gly Val Ser His Ala Val Ala Gly Gly Val Cys Asp Tyr
                 85                  90                  95

Ser Ser Gly Leu Cys Ser Trp Ser Tyr Ala Ala Cys Gly Asp Gly Thr
            100                 105                 110

Ala Val Thr Val Asn
            115

<210> SEQ ID NO 33
<211> LENGTH: 111
<212> TYPE: PRT
<213> ORGANISM: Ginglymostoma cirratum

<400> SEQUENCE: 33

Ala Arg Val Asp Gln Thr Pro Arg Ser Val Thr Lys Glu Thr Gly Glu
  1               5                  10                  15

Ser Leu Thr Ile Asn Cys Val Leu Arg Asp Ala Ser Tyr Ala Leu Gly
                 20                  25                  30

Ser Thr Cys Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
 65                  70                  75                  80

Tyr Arg Cys Gly Val Ser Trp Ala Tyr Ser Cys Asp Tyr Leu Cys Ser
                 85                  90                  95

Asp Glu Tyr Ala Ala Cys Gly Asp Gly Thr Ala Val Thr Val Asn
            100                 105                 110

<210> SEQ ID NO 34
<211> LENGTH: 114
<212> TYPE: PRT
<213> ORGANISM: Ginglymostoma cirratum

<400> SEQUENCE: 34

Ala Arg Val Asp Gln Thr Pro Arg Ser Val Thr Lys Glu Thr Gly Glu
  1               5                  10                  15

Ser Leu Thr Ile Asn Cys Val Leu Arg Asp Ala Ser Tyr Ala Leu Gly
                 20                  25                  30

Ser Thr Cys Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
 65                  70                  75                  80

Tyr Arg Cys Gly Val Ser Leu Gly Ala Arg Tyr Ser Cys Asp Tyr Asn
                 85                  90                  95

Pro Cys Ser Ser Gly Tyr Ala Ala Cys Gly Gly Thr Val Val Thr
            100                 105                 110

Val Asn

<210> SEQ ID NO 35
<211> LENGTH: 113
<212> TYPE: PRT
<213> ORGANISM: Ginglymostoma cirratum
```

```
<400> SEQUENCE: 35

Ala Arg Val Asp Gln Thr Pro Arg Ser Val Thr Lys Glu Thr Gly Glu
 1               5                  10                  15

Ser Pro Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Thr Val Glu Asp Gly Gly Thr
 65                  70                  75                  80

Tyr Arg Cys Gly Val Arg Ile Phe Leu Tyr Ser Cys Asp Tyr Ala Cys
                 85                  90                  95

Ala Leu Asp Gly Tyr Ala Ala Cys Gly Asp Gly Thr Ala Val Thr Val
                100                 105                 110

Asn

<210> SEQ ID NO 36
<211> LENGTH: 113
<212> TYPE: PRT
<213> ORGANISM: Ginglymostoma cirratum

<400> SEQUENCE: 36

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Thr Ile Asn Asp Leu Thr Val Glu Asp Gly Gly Thr
 65                  70                  75                  80

Tyr Arg Cys Gly Ala Arg Pro Val Gly Ser Cys Asp Tyr Asp Leu Cys
                 85                  90                  95

Ser Phe Arg Pro Tyr Ala Ala Cys Gly Asp Gly Thr Ala Val Thr Val
                100                 105                 110

Asn

<210> SEQ ID NO 37
<211> LENGTH: 115
<212> TYPE: PRT
<213> ORGANISM: Ginglymostoma cirratum

<400> SEQUENCE: 37

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Thr Val Glu Asp Gly Gly Thr
 65                  70                  75                  80
```

```
Tyr Arg Cys Gly Val Glu Leu Val Trp Gly Tyr His Ser Cys Asp Tyr
                85                  90                  95

Asp Met Cys Ser Phe Arg Tyr Ala Ala Cys Gly Asp Gly Thr Ala Val
            100                 105                 110

Thr Val Asn
        115

<210> SEQ ID NO 38
<211> LENGTH: 115
<212> TYPE: PRT
<213> ORGANISM: Ginglymostoma cirratum

<400> SEQUENCE: 38

Ala Arg Val Asp Gln Thr Pro Arg Ser Val Thr Lys Glu Thr Gly Glu
  1               5                  10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Gly Gly Thr
 65                 70                  75                  80

Tyr Arg Cys Gly Val Ser Leu Val Trp Ile Gly Tyr Ile Ala Val Thr
                85                  90                  95

Thr Leu Asp Val Leu Leu Arg Ala Ala Cys Gly Asp Gly Thr Ala Val
            100                 105                 110

Thr Val Asn
        115

<210> SEQ ID NO 39
<211> LENGTH: 114
<212> TYPE: PRT
<213> ORGANISM: Ginglymostoma cirratum

<400> SEQUENCE: 39

Ala Arg Val Asp Gln Thr Pro Arg Ser Val Thr Lys Glu Thr Gly Glu
  1               5                  10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Gly Gly Thr
 65                 70                  75                  80

Tyr Arg Cys Gly Leu Ala Tyr Thr Gly Arg Cys Gly Phe Cys Ala Leu
                85                  90                  95

Asp Arg Leu Arg Lys Tyr Ala Asp Cys Gly Asp Gly Thr Ala Val Thr
            100                 105                 110

Val Asn

<210> SEQ ID NO 40
<211> LENGTH: 120
<212> TYPE: PRT
<213> ORGANISM: Ginglymostoma cirratum

<400> SEQUENCE: 40
```

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Gly Gly Thr
65                  70                  75                  80

Tyr Arg Cys Gly Val Cys His Arg Ile Ala Gly Val Glu Ile Ala Val
                85                  90                  95

Thr Gln Val Cys Ala Leu Asn Arg Met Tyr Asn Tyr Ala Ala Cys Gly
                100                 105                 110

Asp Gly Thr Ala Val Thr Val Asn
            115                 120

<210> SEQ ID NO 41
<211> LENGTH: 114
<212> TYPE: PRT
<213> ORGANISM: Ginglymostoma cirratum

<400> SEQUENCE: 41

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Ile Glu Asp Gly Gly Thr
65                  70                  75                  80

Tyr Arg Cys Gly Gln Leu Glu Trp Ser Pro Ala Val Thr Thr Ser Pro
                85                  90                  95

Ala Val Leu Ser Arg His Ala Ala Cys Gly Asp Gly Thr Ala Val Thr
                100                 105                 110

Val Asn

<210> SEQ ID NO 42
<211> LENGTH: 114
<212> TYPE: PRT
<213> ORGANISM: Ginglymostoma cirratum

<400> SEQUENCE: 42

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Gly Gly Thr
65                  70                  75                  80

```
Tyr Arg Cys Gly Val Ser Val Tyr Ser Trp Cys Pro Thr Val Thr Gly
                85                  90                  95
Met Val Cys Ser Pro Tyr Ala Ala Cys Gly Gly Gly Thr Val Val Thr
            100                 105                 110
Val Asn

<210> SEQ ID NO 43
<211> LENGTH: 114
<212> TYPE: PRT
<213> ORGANISM: Ginglymostoma cirratum

<400> SEQUENCE: 43

Ala Arg Val Asp Gln Thr Pro Arg Ser Val Thr Lys Glu Thr Gly Glu
  1               5                  10                  15
Ser Leu Thr Ile Asn Cys Val Leu Arg Asp Ala Ser Tyr Ala Leu Gly
                20                  25                  30
Ser Thr Cys Trp Tyr Arg Lys Lys Ser Gly Ser Thr Asn Glu Glu Ser
            35                  40                  45
Ile Ser Lys Gly Gly Arg Tyr Val Glu Thr Val Asn Ser Gly Ser Lys
        50                  55                  60
Ser Phe Ser Leu Arg Ile Asn Asp Leu Thr Val Glu Asp Gly Gly Thr
 65                  70                  75                  80
Tyr Arg Cys Gly Val Gly Gly Ala Tyr Ser Cys Val Thr Thr Tyr Arg
                85                  90                  95
Gly Cys Ala Leu Tyr Tyr Ala Ala Cys Gly Asp Gly Thr Ala Val Thr
            100                 105                 110
Val Asn

<210> SEQ ID NO 44
<211> LENGTH: 113
<212> TYPE: PRT
<213> ORGANISM: Ginglymostoma cirratum

<400> SEQUENCE: 44

Ala Arg Val Asp Gln Thr Pro Arg Ser Val Thr Lys Glu Thr Gly Glu
  1               5                  10                  15
Ser Leu Thr Ile Asn Cys Val Arg Arg Asp Ala Thr Ser Val Leu Gly
                20                  25                  30
Ala Thr Cys Trp Tyr Arg Lys Lys Ser Gly Ser Thr Asn Glu Glu Ser
            35                  40                  45
Ile Ser Lys Gly Gly Arg Tyr Val Glu Thr Val Asn Ser Gly Ser Lys
        50                  55                  60
Ser Phe Ser Leu Arg Ile Asn Asp Leu Thr Val Glu Asp Gly Gly Thr
 65                  70                  75                  80
Tyr Arg Cys Ala Val Ser Ser Ile Ala Ile Arg Cys Asp His Ala Glu
                85                  90                  95
Leu Cys Ser Arg Tyr Gly Ala Cys Gly Asp Gly Thr Ala Val Thr Val
            100                 105                 110
Asn

<210> SEQ ID NO 45
<211> LENGTH: 114
<212> TYPE: PRT
<213> ORGANISM: Ginglymostoma cirratum

<400> SEQUENCE: 45

Ala Arg Val Asp Gln Thr Pro Arg Ser Val Thr Lys Glu Thr Gly Glu
```

```
                1               5                   10                  15
            Ser Leu Thr Ile Asn Cys Val Leu Arg Asp Ser Asn Cys Ala Leu Ser
                            20                  25                  30

Ser Thr Tyr Trp Tyr Arg Lys Lys Ser Gly Ser Thr Asn Glu Glu Ser
                            35                  40                  45

Ile Ser Lys Gly Gly Arg Tyr Val Glu Thr Val Asn Ser Gly Ser Lys
                            50                  55                  60

Ser Phe Ser Leu Arg Ile Asn Asp Leu Thr Val Glu Asp Gly Gly Thr
                65                      70                  75                      80

Tyr Arg Cys Gly Val Ala Ala Thr Ile Gln Tyr Ser Cys Asp Arg
                            85                  90                  95

Leu Cys Ser Trp Asp Phe Ala Val Cys Gly Asp Gly Thr Ala Val Thr
                            100                 105                 110

Val Asn

<210> SEQ ID NO 46
<211> LENGTH: 110
<212> TYPE: PRT
<213> ORGANISM: Ginglymostoma cirratum

<400> SEQUENCE: 46

Ala Arg Val Asp Gln Thr Pro Arg Ser Val Thr Lys Glu Thr Gly Glu
                1               5                   10                  15

Ser Leu Thr Ile Asn Cys Val Leu Arg Asp Ala Ser Tyr Phe Val Gly
                            20                  25                  30

Ser Thr Cys Trp Trp Ala Ile Lys Gln Gly Ser Thr Asn Thr Glu Thr
                            35                  40                  45

Ile Ser Lys Gly Gly Arg Tyr Val Glu Thr Val Asn Ser Gly Ser Lys
                            50                  55                  60

Ser Phe Ser Leu Arg Ile Asn Gly Leu Lys Val Glu Asp Ser Trp Thr
                65                      70                  75                      80

Tyr Arg Cys Lys Ala Tyr Thr Glu Pro Lys Thr Arg Arg Leu Ile Lys
                            85                  90                  95

Cys Cys Arg Glu Tyr Gly Asp Gly Thr Ala Val Thr Val Asn
                            100                 105                 110

<210> SEQ ID NO 47
<211> LENGTH: 112
<212> TYPE: PRT
<213> ORGANISM: Ginglymostoma cirratum

<400> SEQUENCE: 47

Ala Arg Val Asp Gln Thr Pro Arg Ser Val Thr Lys Glu Thr Gly Glu
                1               5                   10                  15

Ser Leu Thr Ile Asn Cys Val Leu Arg Asp Lys Asp Cys Ala Glu Ser
                            20                  25                  30

Ser Ala Ser Trp Tyr Arg Lys Lys Ser Gly Ser Thr Asn Glu Glu Ser
                            35                  40                  45

Ile Ser Lys Gly Gly Arg Tyr Val Glu Thr Val Asn Ser Gly Ser Lys
                            50                  55                  60

Ser Phe Ser Leu Arg Ile Asn Asp Leu Thr Val Glu Asp Ser Gly Thr
                65                      70                  75                      80

Tyr Arg Cys Lys Val Pro Ser Arg Tyr Ser Tyr Asp Cys Val Arg Phe
                            85                  90                  95

Glu Leu Ile Asp Asp Val Tyr Gly Asp Gly Thr Ala Val Thr Val Asn
                            100                 105                 110
```

<210> SEQ ID NO 48
<211> LENGTH: 108
<212> TYPE: PRT
<213> ORGANISM: Ginglymostoma cirratum

<400> SEQUENCE: 48

Ala Arg Val Asp Gln Thr Pro Lys Thr Val Thr Lys Glu Thr Gly Glu
1               5                   10                  15

Ser Leu Thr Ile Asn Cys Val Leu Ser Asp Thr Ser Cys Ala Trp Asp
            20                  25                  30

Ser Thr Tyr Trp Tyr Arg Lys Lys Leu Gly Ser Thr Asn Glu Glu Ser
        35                  40                  45

Thr Ser Lys Gly Gly Arg Tyr Val Glu Thr Val Asn Ser Glu Ser Thr
    50                  55                  60

Ser Phe Ser Leu Arg Ile Asn Asp Leu Thr Val Glu Asp Ser Gly Thr
65                  70                  75                  80

Tyr Arg Cys Arg Ala Glu Leu Tyr Cys Gly Ala Glu Leu Asp Ser Phe
                85                  90                  95

Asp Glu Tyr Gly Asp Gly Thr Ala Val Thr Val Asn
            100                 105

<210> SEQ ID NO 49
<211> LENGTH: 104
<212> TYPE: PRT
<213> ORGANISM: Ginglymostoma cirratum

<400> SEQUENCE: 49

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Ser Arg Cys Ser Thr Asn Leu Ile Gly Tyr Gly
                85                  90                  95

Gly Gly Thr Val Val Thr Val Asn
            100

<210> SEQ ID NO 50
<211> LENGTH: 108
<212> TYPE: PRT
<213> ORGANISM: Ginglymostoma cirratum

<400> SEQUENCE: 50

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Ala Cys Lys Ala Glu Gly Met Asp Arg Glu Ile Arg Leu Asn Cys
                85                  90                  95

Val Ile Tyr Gly Gly Gly Thr Val Val Thr Val Asn
            100                 105

<210> SEQ ID NO 51
<211> LENGTH: 113
<212> TYPE: PRT
<213> ORGANISM: Ginglymostoma cirratum

<400> SEQUENCE: 51

Ala Arg Val Asp Gln Thr Pro Gln Thr Ile Thr Lys Glu Thr Gly Asp
1               5                   10                  15

Thr Leu Thr Ile Asn Cys Val Leu Arg Asp Ser Asn Cys Ala Leu Ser
            20                  25                  30

Asp Met Tyr Trp Ser Arg Lys Lys Ser Gly Ser Thr His Glu Glu Asn
            35                  40                  45

Ile Ala Lys Glu Gly Arg Tyr Val Glu Thr Phe Asn Arg Ala Ser Lys
        50                  55                  60

Ser Ser Ser Leu Arg Ile Asn Asp Leu Thr Val Ala Asp Ser Gly Thr
65                  70                  75                  80

Tyr Arg Cys Arg Leu Asp Leu Val Cys Asp Glu Thr Ala Tyr Gln Asp
                85                  90                  95

Glu Leu Glu Phe Asp Asp Ile Tyr Gly Asp Gly Thr Ala Val Thr Val
            100                 105                 110

Asn

<210> SEQ ID NO 52
<211> LENGTH: 113
<212> TYPE: PRT
<213> ORGANISM: Ginglymostoma cirratum

<400> SEQUENCE: 52

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Glu Gly Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Gly Gly Thr
65                  70                  75                  80

Tyr Arg Cys Gly Leu Gly Val Ala Gly Tyr Cys Asp Tyr Ala Leu
                85                  90                  95

Cys Ser Ser Arg Tyr Ala Glu Cys Gly Asp Gly Thr Ala Val Thr Val
            100                 105                 110

Asn

<210> SEQ ID NO 53
<211> LENGTH: 339
<212> TYPE: DNA
<213> ORGANISM: Ginglymostoma cirratum

<400> SEQUENCE: 53

```
gctcgagtgg accaaacacc gagatcagta acaaaggaga cgggcgaatc actgaccatc    60
aactgtgtcc tacgagatgc gagctatgca ttgggcagca cgtgctggta tcgaaaaaaa   120
tcgggcgaag gaaacgagga gagcatatcg aaaggtggac gatatgttga aacagttaac   180
agcggatcaa agtccttttc tttgagaatt aatgatctaa cagttgaaga cggtggcacg   240
tatcgttgcg gtctcggggt agctggaggg tactgtgact acgctctgtg ctcttcccgc   300
tatgctgaat gcggagatgg cactgccgtg actgtgaat                          339
```

<210> SEQ ID NO 54
<211> LENGTH: 339
<212> TYPE: DNA
<213> ORGANISM: Ginglymostoma cirratum

<400> SEQUENCE: 54

```
cgagctcacc tggtttgtgg ctctagtcat tgtttcctct gcccgcttag tgactggtag    60
ttgacacagg atgctctacg ctcgatacgt aacccgtcgt gcacgaccat agcttttttt   120
acgccgcttc ctttgctcct ctcgtatagc tttccacctg ctatacaact ttgtcaattg   180
tcgcctagtt tcaggaaaag aaactcttaa ttactagatt gtcaacttct gccaccgtgc   240
atagcaacgc cagagcccca tcgacctccc atgcactga tgcgagacac gagaagggcg    300
atacgactta cgcctctacc gtgacggcac tgacactta                          339
```

<210> SEQ ID NO 55
<211> LENGTH: 113
<212> TYPE: PRT
<213> ORGANISM: Ginglymostoma cirratum

<400> SEQUENCE: 55

```
Ala Arg Val Asp Gln Thr Pro Arg Ser Val Thr Lys Glu Thr Gly Glu
  1               5                  10                  15

Ser Leu Thr Ile Asn Cys Val Leu Arg Asp Ala Ser Tyr Ala Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Thr Val Glu Asp Gly Gly Thr
 65                  70                  75                  80

Tyr Arg Cys Gly Leu Gly Val Ala Gly Gly Tyr Cys Asp Tyr Ala Leu
                 85                  90                  95

Cys Ser Ser Arg Tyr Ala Glu Cys Gly Asp Gly Thr Ala Val Thr Val
                100                 105                 110

Asn
```

<210> SEQ ID NO 56
<211> LENGTH: 339
<212> TYPE: DNA
<213> ORGANISM: Ginglymostoma cirratum

<400> SEQUENCE: 56

```
gctcgagtgg accaaacacc gagatcagta acaaaggaga cgggcgaatc actgaccatc    60
aactgtgtcc tacgagatgc gagctatgca ttgggcagca cgtgctggta tcgaaaaaaa   120
tcgggctcaa caaacgagga gagcatatcg aaaggtggac gatatgttga aacagttaac   180
agcggatcaa agtccttttc tttgagaatt aatgatctaa cagttgaaga cggtggcacg   240
```

```
tatcgttgcg gtctcggggt agctggaggg tactgtgact acgctctgtg ctcttcccgc    300
tatgctgaat gcggagatgg cactgccgtg actgtgaat                           339
```

<210> SEQ ID NO 57
<211> LENGTH: 339
<212> TYPE: DNA
<213> ORGANISM: Ginglymostoma cirratum

<400> SEQUENCE: 57

```
cgagctcacc tggtttgtgg ctctagtcat tgtttcctct gcccgcttag tgactggtag    60
ttgacacagg atgctctacg ctcgatacgt aacccgtcgt gcacgaccat agcttttttt    120
agcccgagtt gtttgctcct ctcgtatagc tttccacctg ctatacaact tgtcaattg     180 tcgcctagtt tcaggaaaag aaactcttaa ttactagatt gtcaacttct gccaccgtgc    240
atagcaacgc cagagcccca tcgacctccc atgcactga tgcgagacac gagaagggcg     300
atacgactta cgcctctacc gtgacggcac tgacactta                           339
```

<210> SEQ ID NO 58
<211> LENGTH: 114
<212> TYPE: PRT
<213> ORGANISM: Ginglymostoma cirratum

<400> SEQUENCE: 58

```
Ala Arg Val Asp Gln Thr Pro Arg Ser Val Thr Lys Glu Thr Gly Glu
 1               5                  10                  15

Ser Leu Thr Ile Asn Cys Val Leu Arg Asp Ala Asn Tyr Ala Leu Gly
            20                  25                  30

Ser Thr Cys Trp Tyr Arg Lys Lys Ser Gly Ser Thr Asn Trp Asp Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Arg Glu Gly Arg Tyr His Met Asp Ser Cys Asp Tyr
                85                  90                  95

Ser Arg Cys Arg Tyr Tyr Ala Ala Cys Gly Asp Gly Thr Ala Val Thr
            100                 105                 110

Val Asn
```

<210> SEQ ID NO 59
<211> LENGTH: 341
<212> TYPE: DNA
<213> ORGANISM: Ginglymostoma cirratum

<400> SEQUENCE: 59

```
gctcgagtgg accaaacacg agatcagtaa caaaggagac gggcgaatca ctgaccatca    60
actgtgtcct acgagatgcg aactatgcat gggcagcac gttggtat cgaaaaaat        120 cgggctcaac aaactgggac agcatatcga aggtggacg atatgttgaa acagttaaca    180
gcggatcaaa gtccttttct ttgagaatta atgatctaac agttgaagac ggtggcacgt    240
atcgttgcgg tcgagagggc cggtatcata tggatagctg tgactacagt cggtgtcgct    300
actatgctgc atgcggagat ggcactgccg tgactgtgaa t                        341
```

<210> SEQ ID NO 60
<211> LENGTH: 342
<212> TYPE: DNA

<213> ORGANISM: Ginglymostoma cirratum

<400> SEQUENCE: 60

```
cgagctcacc tggtttgtgg ctctagtcat tgtttcctct gcccgcttag tgactggtag      60
ttgacacagg atgctctacg cttgatacgt aacccgtcgt gcacaaccat agcttttttt     120
agcccgagtt gtttgaccct gtcgtatagc tttccacctg ctatacaact tgtcaattg      180
tcgcctagtt tcaggaaaag aaactcttaa ttactagatt gtcaacttct gccaccgtgc     240
atagcaacgc cagctctccc ggccatagta tacctatcga cactgatgtc agccacagcg     300
atgatacgac gtacgcctct accgtgacgg cactgacact ta                        342
```

<210> SEQ ID NO 61
<211> LENGTH: 114
<212> TYPE: PRT
<213> ORGANISM: Ginglymostoma cirratum

<400> SEQUENCE: 61

Ala Arg Val Asp Gln Thr Pro Arg Ser Val Thr Lys Val Ala Gly Glu
 1               5                   10                  15

Ser Leu Thr Ile Asn Cys Val Leu Arg Asp Ala Asn Tyr Pro Leu Gly
             20                  25                  30

Ser Thr Cys Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
     50                  55                  60

Ser Phe Ser Leu Arg Ile Asn Asp Leu Thr Val Glu Asp Gly Gly Thr
 65                  70                  75                  80

Tyr Arg Cys Gly Arg Glu Gly Arg Tyr His Met Asp Ser Cys Asp Tyr
                 85                  90                  95

Ser Arg Cys Arg Tyr Tyr Gly Ala Cys Gly Asp Gly Thr Ala Val Thr
            100                 105                 110

Val Asn

<210> SEQ ID NO 62
<211> LENGTH: 342
<212> TYPE: DNA
<213> ORGANISM: Ginglymostoma cirratum

<400> SEQUENCE: 62

```
gctcgagtgg accaaacacc gagatcagta acaaaggttg cgggcgaatc actgaccatc      60
aactgtgtcc tacagagatgc gaactaccca ttgggcagta cgtgctggta tcgaaaaaaa     120
tcgggctcaa caaacgagga gagcatatcg aaaggtggac gatatgttga acagttaac      180
agccgatcaa agtccttttc tttgagaatt aatgatctaa cagttgaaga cggtggcacg     240
tatcgttgcg aagagaggg ccggtatcat atggatagct gtgactacag tcggtgtcgc      300
tactatggtg catgcggaga tggcactgcc gtgactgtga at                        342
```

<210> SEQ ID NO 63
<211> LENGTH: 342
<212> TYPE: DNA
<213> ORGANISM: Ginglymostoma cirratum

<400> SEQUENCE: 63

```
cgagctcacc tggtttgtgg ctctagtcat tgtttccaac gcccgcttag tgactggtag      60
ttgacacagg atgctctacg cttgatgggt aacccgtcat gcacgaccat agcttttttt     120
```

```
agcccgagtt gtttgctcct ctcgtatagc tttccacctg ctatacaact ttgtcaattg    180
tcgcctagtt tcaggaaaag aaactcttaa ttactagatt gtcaacttct gccaccgtgc    240
atagcaacgc cttctctccc ggccatagta tacctatcga cactgatgtc agccacagcg    300
atgataccac gtacgcctct accgtgacgg cactgacact ta                       342
```

<210> SEQ ID NO 64
<211> LENGTH: 46
<212> TYPE: DNA
<213> ORGANISM: Ginglymostoma cirratum

<400> SEQUENCE: 64

```
ataatcaagc ttgcggccgc attcacagtc acgacagtgc cacctc                    46
```

<210> SEQ ID NO 65
<211> LENGTH: 46
<212> TYPE: DNA
<213> ORGANISM: Ginglymostoma cirratum

<400> SEQUENCE: 65

```
ataatcaagc ttgcggccgc attcacagtc acggcagtgc catctc                    46
```

<210> SEQ ID NO 66
<211> LENGTH: 39
<212> TYPE: DNA
<213> ORGANISM: Ginglymostoma cirratum

<400> SEQUENCE: 66

```
ataataagga attccatggc tcgagtggac caaacaccg                            39
```

<210> SEQ ID NO 67
<211> LENGTH: 16
<212> TYPE: DNA
<213> ORGANISM: Artificial sequence
<220> FEATURE:
<223> OTHER INFORMATION: M13 reverse primer

<400> SEQUENCE: 67

```
ttcacacagg aaacag                                                     16
```

<210> SEQ ID NO 68
<211> LENGTH: 21
<212> TYPE: DNA
<213> ORGANISM: Artificial sequence
<220> FEATURE:
<223> OTHER INFORMATION: HuCk forward primer

<400> SEQUENCE: 68

```
gaagatgaag acagatggtg c                                               21
```

<210> SEQ ID NO 69
<211> LENGTH: 17
<212> TYPE: PRT
<213> ORGANISM: Artificial sequence
<220> FEATURE:
<223> OTHER INFORMATION: LMB3 primer

<400> SEQUENCE: 69

Cys Ala Gly Gly Ala Ala Ala Cys Ala Gly Cys Thr Ala Thr Gly Ala
 1               5                  10                  15

Cys

<210> SEQ ID NO 70

```
<211> LENGTH: 17
<212> TYPE: PRT
<213> ORGANISM: Artificial sequence
<220> FEATURE:
<223> OTHER INFORMATION: pHEN primer

<400> SEQUENCE: 70

Cys Thr Ala Thr Gly Cys Gly Gly Cys Cys Cys Cys Ala Thr Thr Cys
 1               5                  10                  15

Ala
```

The invention claimed is:

1. A process for the production of an antigen specific antigen binding domain comprising the steps of:
   (a) immunizing a member of the Elasmobranchii subclass with a specific antigen such that the binding domain is somatically matured;
   (b) isolating lymphocytes from the immunizing species;
   (c) isolating RNA from the lymphocytes;
   (d) amplifying DNA sequences encoding the antigen specific antigen binding domain by PCR;
   (e) cloning the amplified DNA into a display vector;
   (f) transforming a host to produce a library;
   (g) selecting the desired clones from the library;
   (h) isolating and purifying the antigen specific antigen binding domain from these clones;
   (i) cloning the DNA sequences encoding the antigen specific antigen binding domain into an expression vector;
   (j) transforming a host with the expression vector;
   (k) culturing the host; and
   (l) isolating the antigen specific antigen binding domain so that the antigen specific antigen binding domain is produced.

2. A process according to claim 1 wherein the member is a shark or dog fish.

3. A process according to claim 1 wherein before step (d) the cDNA of the antigen specific antigen binding domain is generated.

4. A process according to claim 1 wherein the restriction enzymes are used to digest the amplified DNA sequences encoding the antigen specific antigen binding domain.

5. A process according to claim 4 wherein the restriction enzymes are NcoI and NotI.

6. A process according to claim 1 wherein the display vector is any phagemid vector.

7. A process according to claim 1 wherein the expression vector is a soluble expression vector.

8. A process for the production of an antigen specific antigen binding domain comprising:
   (a) transforming a host with an expressible DNA sequence encoding an antigen specific antigen binding domain, wherein the antigen specific antigen binding domain is derived from a variable region of the immunoglobulin isotype Novel Antigen Receptor (NAR) from a member of the Elasmobranchii subclass immunized with a specific antigen;
   (b) culturing the host so that the antigen specific antigen binding domain is expressed; and
   (c) isolating the antigen specific antigen binding domain, thereby producing an antigen specific antigen binding domain.

9. The process of claim 8 wherein the member is a shark or dog fish.

10. The process of claim 8 wherein the transformed host is a prokaryote or a lower eukaryote.

11. The process of claim 10 wherein the prokaryote host is *Escherichia coli*.

12. The process of claim 8 wherein the expressible DNA sequence is in the form of a phagemid vector.

13. The process of claim 8 wherein the member is a nurse shark.

14. The process of claim 8 wherein the antigen specific antigen binding domain is specific for the antigen.

15. The process of claim 8 wherein the antigen specific antigen binding domain is monoclonal.

* * * * *